(12) United States Patent
Billinton et al.

(10) Patent No.: US 8,252,833 B2
(45) Date of Patent: Aug. 28, 2012

(54) BENZO (F) ISOINDOL-2-YLPHENYL ACETIC ACID DERIVATIVES AS EP$_4$ RECEPTOR AGONISTS

(75) Inventors: Andrew Billinton, Harlow (GB); Nicholas Maughan Clayton, Harlow (GB); Gerard Martin Paul Giblin, Harlow (GB); Mark Patrick Healy, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 1024 days.

(21) Appl. No.: 12/278,019

(22) PCT Filed: Feb. 1, 2007

(86) PCT No.: PCT/EP2007/050992
§ 371 (c)(1),
(2), (4) Date: Aug. 1, 2008

(87) PCT Pub. No.: WO2007/088190
PCT Pub. Date: Aug. 9, 2007

(65) Prior Publication Data
US 2011/0201663 A1    Aug. 18, 2011

(30) Foreign Application Priority Data
Feb. 3, 2006  (GB) ................................ 0602237.0
May 5, 2006   (GB) ................................ 0608976.7

(51) Int. Cl.
*A01N 43/48*   (2006.01)
*A61K 31/40*   (2006.01)
*C07D 207/00*  (2006.01)
*C07D 295/00*  (2006.01)
*C07D 405/00*  (2006.01)

(52) U.S. Cl. .................. 514/411; 548/400; 548/563

(58) Field of Classification Search .................. None
See application file for complete search history.

(56) References Cited

U.S. PATENT DOCUMENTS

| | | | |
|---|---|---|---|
| 6,861,441 B1 * | 3/2005 | Clayton et al. | 514/411 |
| 7,166,631 B2 * | 1/2007 | Congreve et al. | 514/411 |
| 7,718,689 B2 * | 5/2010 | Healy et al. | 514/411 |
| 7,732,622 B2 * | 6/2010 | Congreve et al. | 548/529 |

FOREIGN PATENT DOCUMENTS

| | | |
|---|---|---|
| WO | 0250032 A | 6/2002 |
| WO | 0250033 A | 6/2002 |
| WO | 02064564 A | 8/2002 |

OTHER PUBLICATIONS

Patani GA, LaVoie EJ.Chem Rev ."Bioisosterism: A Rational Approach in Drug Design." Chem Rev. Dec. 19, 1996;96(8):3147-3176.*

* cited by examiner

*Primary Examiner* — Jeffrey S. Lundgren
*Assistant Examiner* — William Lee
(74) *Attorney, Agent, or Firm* — Robert (Steve) Thomas

(57) ABSTRACT

A compound of formula (I) or a pharmaceutically acceptable derivative thereof,

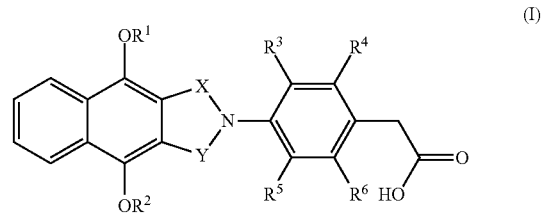

wherein, $R^1$ $R^2$ $R^3$, $R^4$, $R^5$, $R^6$, X and Y are as defined in the specification; a process for preparing such compounds; a pharmaceutical composition comprising such compounds; and the use of such compounds in medicine.

11 Claims, 2 Drawing Sheets

Figure 1 - The effect of combining Example 9 (0.1 mg/kg) and paracetamol (60 mg/kg) alone and in combination on FCA-induced hypersensitivity.
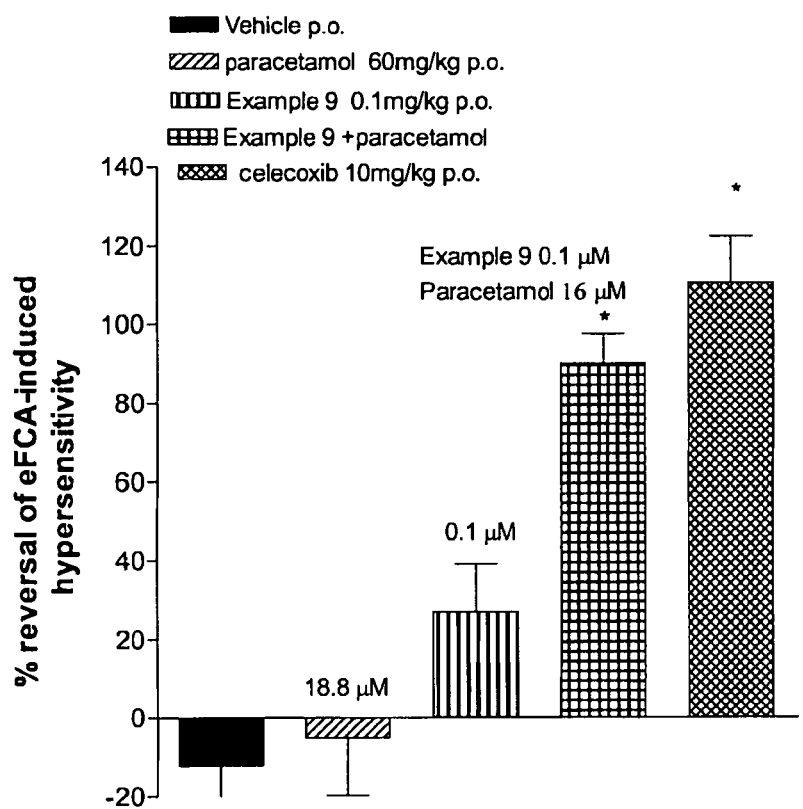

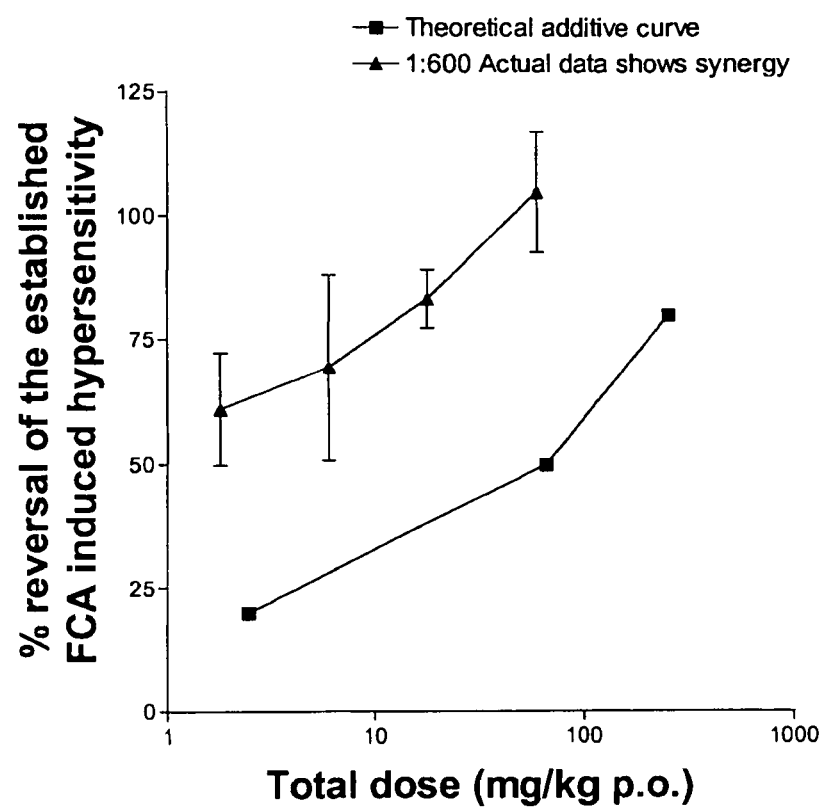
Figure 2 – Theoretical additive dose response curve vs. actual observed dose response curve for Example 9 + paracetamol combination

BENZO (F) ISOINDOL-2-YLPHENYL ACETIC ACID DERIVATIVES AS EP$_4$ RECEPTOR AGONISTS

CROSS-REFERENCE TO RELATED APPLICATIONS

This application is filed pursuant to 35 USC 371 as a United States National Phase Application of International Patent Application Serial No. PCT/EP2007/050992 filed on Feb. 1, 2007, which claims priority from 0602237.0 filed Feb. 3, 2006 and 0608976.7 filed on May 5, 2006 in the United Kingdom.

FIELD OF THE INVENTION

This invention relates to naphthalene derivatives, to processes for their preparation, to pharmaceutical compositions containing them and to their use in medicine.

The compounds of the present invention are EP$_4$ receptor agonists.

BACKGROUND OF THE INVENTION

A number of review articles describe the characterization and therapeutic relevance of the prostanoid receptors as well as the most commonly used selective agonists and antagonists: *Eicosanoids; From Biotechnology to Therapeutic Applications*, Folco, Samuelsson, Maclouf, and Velo eds, Plenum Press, New York, 1996, chap. 14, 137-154 and Journal of Lipid Mediators and Cell Signalling, 1996, 14, 83-87 and *Prostanoid Receptors, Structure, Properties and Function*, S Narumiya et al, Physiological Reviews 1999, 79(4), 1193-126.

The EP$_4$ receptor is a 7-transmembrane receptor and its natural ligand is the prostaglandin PGE$_2$. PGE$_2$ also has affinity for the other EP receptors (types EP$_1$, EP$_2$ and EP$_3$). The prostanoid EP$_4$ receptor falls into a group of receptors normally associated with elevation of intracellular cyclic adenosine monophosphate (cAMP) levels. The EP$_4$ receptor is associated with smooth muscle relaxation, intraocular pressure, pain (in particular inflammatory, neuropathic and visceral pain), inflammation, neuroprotection, lymphocyte differentiation, bone metabolic processes, allergic activities, promotion of sleep, renal regulation, gastric or enteric mucus secretion and duodenal bicarbonate secretion. The EP$_4$ receptor plays an important role in closure of the ductus arteriosus, vasodepression, inflammation and bone remodeling as reviewed by Narumiya in *Prostaglandins & Other Lipid Mediators* 2002, 68-69 557-73.

A number of publications have demonstrated that PGE$_2$ acting through the EP$_4$ receptor subtype, and EP$_4$ agonists alone, can regulate inflammatory cytokines after an inflammatory stimulus. Takayama et al in the *Journal of Biological Chemistry* 2002, 277(46), 44147-54 showed PGE$_2$ modulates inflammation during inflammatory diseases by suppressing macrophage derived chemokine production via the EP$_4$ receptor. In *Bioorganic & Medicinal Chemistry* 2002, 10(7), 2103-2110, Maruyama et al demonstrate the selective EP$_4$ receptor agonist (ONO-AE1-437) suppresses LPS induced TNF-α in human whole blood whilst increasing the levels of IL-10. An article from *Anesthesiology*, 2002, 97, 170-176 suggests that a selective EP$_4$ receptor agonist (ONO-AE1-329) effectively inhibited mechanical and thermal hyperalgesia and inflammatory reactions in acute and chronic monoarthritis.

Two independent articles from Sakuma et al in *Journal of Bone and Mineral Research* 2000, 15(2), 218-227 and Miyaura et al in *Journal of Biological Chemistry* 2000, 275 (26), 19819-23, report impaired osteoclast formation in cells cultured from EP$_4$ receptor knock-out mice. Yoshida et al in *Proceedings of the National Academy of Sciences of the United States of America* 2002, 99(7), 4580-4585, by use of mice lacking each of the PGE$_2$ receptor EP subtypes, identified EP$_4$ as the receptor that mediates bone formation in response to PGE$_2$ administration. They also demonstrated a selective EP$_4$ receptor agonist (ONO-4819) consistently induces bone formation in wild type mice. Additionally, Terai et al in *Bone* 2005, 37(4), 555-562 have shown the presence of a selective EP$_4$ receptor agonist (ONO-4819) enhanced the bone-inducing capacity of rhBMP-2, a therapeutic cytokine that can induce bone formation.

Further research by Larsen et al shows the effects of PGE$_2$ on secretion in the second part of the human duodenum is mediated through the EP$_4$ receptor (*Acta. Physiol. Scand.* 2005, 185, 133-140). Also, it has been shown a selective EP$_4$ receptor agonist (ONO-AE1-329) can protect against colitis in rats (Nitta et al in *Scandinavian Journal of Immunology* 2002, 56(1), 66-75).

Doré et al in *The European Journal of Neuroscience* 2005, 22(9), 2199-206 have shown that PGE$_2$ can protect neurons against amyloid beta peptide toxicity by acting on EP$_2$ and EP$_4$ receptors. Furthermore Doré has demonstrated in *Brain Research* 2005, 1066(1-2), 71-77 that an EP$_4$ receptor agonist (ONO-AE1-329) protects against neurotoxicity in an acute model of excitotoxicity in the brain.

Woodward et al in Journal of Lipid Mediators 1993, 6(1-3), 545-53 found intraocular pressure could be lowered using selective prostanoid agonists. Two papers in Investigative Ophthalmology & Visual Science have shown the prostanoid EP$_4$ receptor is expressed in human lens epithelial cells (Mukhopadhyay et al 1999, 40(1), 105-12), and suggest a physiological role for the prostanoid EP$_4$ receptor in modulation of flow in the trabecular framework of the eye (Hoyng et al 1999, 40(11), 2622-6).

Compounds exhibiting EP$_4$ receptor binding activity and their uses have been described in, for example, WO98/55468, WO00/18744, WO00/03980, WO00/15608, WO00/16760, WO00/21532, WO01010426, EP0855389, EP0985663, WO02/047669, WO02/50031, WO02/50032, WO02/50033, WO02/064564, WO03/103604, WO03/077910, WO03/086371, WO04/037813, WO04/067524, WO04/085430, US04/142969, WO05/021508, WO05/105733, WO05/105732, WO05/080367, WO05/037812, WO05/116010 and WO06/122403.

Derivatives of indoprofen such as [4-(1-oxo-1,3-dihydro-2H-benzo[f]isoindol-2-yl)phenyl]-2-propionic acid, sodium salt have been described by Rufer et. al. in *Eur. J. Med. Chem.-Chimica Therapeutica*, 1978, 13, 193.

DETAILED DESCRIPTION

The compounds of the present invention have been shown to exhibit advantageous in vivo and in vitro activities when tested in the biological assays described herein. Certain compounds of the invention have also been shown to exhibit advantageous pharmacokinetic profiles in the rat.

The present invention provides compounds of formula (I) and/or pharmaceutically acceptable derivatives thereof,

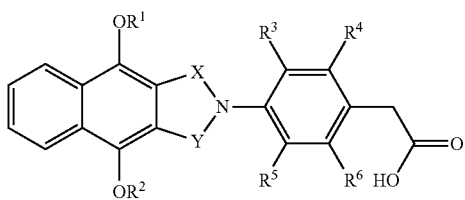

(I)

wherein, $R^1$ and $R^2$ independently represent $C_{1-4}$ alkyl;

$R^3$, $R^4$, $R^5$ and $R^6$ independently represent H or F, provided that at least one of $R^3$ and $R^4$ represents H, at least one of $R^5$ and $R^6$ represents H, and at least one of $R^3$, $R^4$, $R^5$ and $R^6$ represents F; and X and Y independently represent $CH_2$ or C=O, provided that at least one of X and Y represents C=O.

In one embodiment of the invention $R^1$ and $R^2$ are the same and represent $C_{1-4}$ alkyl. In another embodiment of the invention $R^1$ and $R^2$ are independently selected from the group consisting of ethyl, n-propyl and iso-propyl.

In one embodiment of the invention $R^3$ represents H and $R^4$ represents F. In another embodiment of the invention $R^3$ represents F and $R^4$ represents H.

In one embodiment of the invention $R^5$ represents H and $R^6$ represents F. In another embodiment of the invention $R^5$ represents F and $R^6$ represents H.

In one embodiment of the invention $R^3$ represents F and $R^4$, $R^5$ and $R^6$ represent H. In another embodiment of the invention $R^4$ represents F and $R^3$, $R^5$ and $R^6$ represent H. In another embodiment of the invention $R^5$ represents F and $R^3$, $R^4$ and $R^6$ represent H. In a further embodiment of the invention $R^6$ represents F and $R^3$, $R^4$ and $R^5$ represent H.

In one embodiment of the invention $R^3$ and $R^5$ represent F and $R^4$ and $R^6$ represent H.

In one embodiment of the invention X represents $CH_2$ and Y represents C=O. In another embodiment of the invention X represents C=O and Y represents $CH_2$. In another embodiment of the invention both X and Y represent C=O.

In one embodiment of the invention there is provided a subset of compounds of formula (I), of formula (IA) and/or pharmaceutically acceptable derivatives thereof,

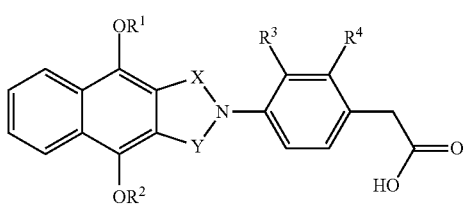

(IA)

wherein, $R^1$ and $R^2$ independently represent $C_{1-4}$ alkyl;

$R^3$ and $R^4$ independently represent H or F provided that they are not the same; and X and Y independently represent $CH_2$ or C=O provided that at least one of X and Y represents C=O.

In another embodiment of the invention there is provided a compound of formula (I) selected from the group consisting of:

{4-[4,9-Bis(ethyloxy)-1,3-dioxo-1,3-dihydro-2H-benzo[f]isoindol-2-yl]-3-fluorophenyl}acetic acid;
{4-[1,3-Dioxo-4,9-bis(propyloxy)-1,3-dihydro-2H-benzo[f]isoindol-2-yl]-3-fluorophenyl}acetic acid;
(4-{4,9-Bis(1-methylethoxy)-1,3-dioxo-1,3-dihydro-2H-benzo[f]isoindol-2-yl}-3-fluorophenyl)acetic acid;
{4-[4,9-Bis(ethyloxy)-1-oxo-1,3-dihydro-2H-benzo[f]isoindol-2-yl]-3-fluorophenyl}acetic acid;
{4-[4,9-Bis(ethyloxy)-1-oxo-1,3-dihydro-2H-benzo[f]isoindol-2-yl]-2-fluorophenyl}acetic acid;
{2-Fluoro-4-[1-oxo-4,9-bis(propyloxy)-1,3-dihydro-2H-benzo[f]isoindol-2-yl]phenyl}acetic acid;
(4-{4,9-Bis(1-methylethoxy)-1-oxo-1,3-dihydro-2H-benzo[f]isoindol-2-yl}-2-fluorophenyl)acetic acid;
{3-Fluoro-4-[1-oxo-4,9-bis(propyloxy)-1,3-dihydro-2H-benzo[f]isoindol-2-yl]phenyl}acetic acid; and
(4-{4,9-Bis(1-methylethoxy)-1-oxo-1,3-dihydro-2H-benzo[f]isoindol-2-yl}-3-fluorophenyl)acetic acid;
{4-[4,9-Bis(ethyloxy)-1,3-dioxo-1,3-dihydro-2H-benzo[f]isoindol-2-yl]-3,5-difluorophenyl}acetic acid;
{-4-[4,9-Bis(ethyloxy)-1-oxo-1,3-dihydro-2H-benzo[f]isoindol-2-yl]-3,5-difluorophenyl}acetic acid; and/or a pharmaceutically acceptable derivative thereof.

In another embodiment of the invention there is provided a compound of formula (I) being {4-[4,9-bis(ethyloxy)-1-oxo-1,3-dihydro-2H-benzo[f]isoindol-2-yl]-2-fluorophenyl}acetic acid (IB),

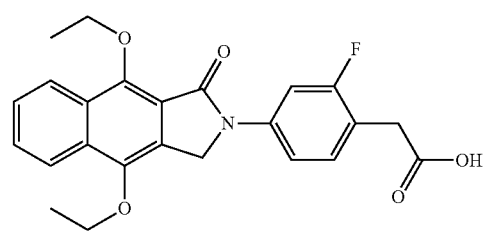

(IB)

or a pharmaceutically acceptable derivative thereof.

The present invention covers all combinations of the embodiments described herein.

As used herein, the term '$C_{1-4}$ alkyl' includes straight chain and branched chain alkyl groups containing 1 to 4 carbon atoms, such as methyl, ethyl, n-propyl, iso-propyl, n-butyl and iso-butyl. The term '$C_{1-6}$ alkyl' may be interpreted accordingly.

As used herein, F means fluoro.

By pharmaceutically acceptable derivative is meant any pharmaceutically acceptable salt, solvate or ester, or salt or solvate of such ester of the compounds of formula (I), or any other compound which upon administration to the recipient is capable of providing (directly or indirectly) a compound of formula (I) or an active metabolite or residue thereof. In one embodiment of the invention pharmaceutically acceptable derivative means salt, solvate or ester, or salt or solvate of such ester. In another embodiment of the invention pharmaceutically acceptable derivative means salt or ester, or salt of such ester.

It will be appreciated that, for pharmaceutical use, the salts referred to above will be the pharmaceutically acceptable salts, but other salts may find use, for example in the preparation of compounds of formula (I) and the pharmaceutically acceptable salts thereof.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropyl amine, tris(hydroxymethyl)aminomethane, and the like. Salts may also be formed from basic ion exchange resins, for example polyamine resins.

In one embodiment of the invention there is provided the sodium salt of {4-[4,9-bis(ethyloxy)-1-oxo-1,3-dihydro-2H-benzo[f]isoindol-2-yl]-2-fluorophenyl}acetic acid. In another embodiment of the invention there is provided the potassium salt of {-4-[4,9-bis(ethyloxy)-1-oxo-1,3-dihydro-2H-benzo[f]isoindol-2-yl]-2-fluorophenyl}acetic acid. In another of the invention there is provided the cholinate salt of {-4-[4,9-bis(ethyloxy)-1-oxo-1,3-dihydro-2H-benzo[f]isoindol-2-yl]-2-fluorophenyl}acetic acid.

It will be appreciated that the compounds of formula (I) may be produced in vivo by metabolism of a suitable prodrug. Such prodrugs may be for example physiologically acceptable metabolically labile esters of compounds of formula (I). These may be formed by esterification of the carboxylic acid group in the parent compound of formula (I) with, where appropriate, prior protection of any other reactive groups present in the molecule followed by deprotection if required. Examples of such metabolically labile esters include $C_{1-4}$alkyl esters e.g. methyl ethyl or t-butyl esters esters, $C_{3-6}$ alkenyl esters e.g. allyl substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl, 1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

It is to be understood that the present invention encompasses all isomers of the compounds of formula (I) and their pharmaceutically acceptable derivatives, including all geometric, tautomeric and optical forms, and mixtures thereof (e.g. racemic mixtures).

Since the compounds of formula (I) are intended for use in pharmaceutical compositions, it will be understood that they are each provided in substantially pure form, for example at least 50% pure, at least 75% pure and at least 95% pure (% are on a wt/wt basis). Impure preparations of the compounds of formula (I) may be used for preparing the more pure forms used in the pharmaceutical compositions. Although the purity of intermediate compounds of the present invention is less critical, it will be readily understood that the substantially pure form is preferred as for the compounds of formula (I). Whenever possible, the compounds of the present invention are obtained in crystalline form.

When some of the compounds of this invention are allowed to crystallise or are recrystallised from organic solvents, solvent of crystallisation may be present in the crystalline product. This invention includes within its scope such solvates, including solvates of the free acid molecule and solvates of salts derived from the free acid molecule. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation. This invention also includes within its scope anhydrous forms of the compounds of formula (I).

In addition, different crystallisation conditions may lead to the formation of different polymorphic forms of crystalline products. This invention includes within its scope all polymorphic forms of the compounds of formula (I).

The present invention also includes within its scope all isotopically-labelled compounds of formula (I). Such compounds are identical to those recited above except that one or more atoms therein are replaced by an atom having an atomic mass or mass number different from the atomic mass or mass number usually found in nature. Examples of isotopes that can be incorporated into compounds of formula (I) and pharmaceutically acceptable derivatives thereof include isotopes of hydrogen, carbon, nitrogen, oxygen and fluorine, such as 2H, 3H, 11C, 13C, 14C, 15N, 17O, 18O and 18F.

Isotopically-labelled compounds of formula (I), for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and are useful in brain imaging. Further substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula (I) may be prepared by carrying out the synthetic procedures disclosed in the Schemes and/or in the Examples below, by substituting a readily available isotopically labelled reagent for a non-isotopically labelled reagent.

The compounds of formula (I) are $EP_4$ receptor agonists and may therefore be useful in treating $EP_4$ receptor mediated diseases.

In particular the compounds of formula (I) may be useful in the treatment of pain, for example, chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of formula (I) may be particularly useful in the treatment of neuropathic pain and symptoms associated therewith. Neuropathic pain syndromes include: diabetic neuropathy; sciatica; non-specific lower back pain; multiple sclerosis pain; fibromyalgia; HIV-related neuropathy; postherpetic neuralgia; trigeminal neuralgia; and pain resulting from physical trauma, amputation, cancer, toxins or chronic inflammatory conditions. Symptoms of neuropathic pain include spontaneous shooting and lancinating pain, or ongoing, burning pain. In addition, there is included pain associated with normally non-painful sensations such as "pins and needles" (paraesthesias and dysesthesias), increased sensitivity to touch (hyperesthesia), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of formula (I) may also be useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome, pigeon fancier's disease, farmer's lung, COPD; gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease, diarrhoea, constipation); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of formula (I) may also be useful in the treatment of immunological diseases such as autoimmune diseases, immunological deficiency diseases or organ transplantation. The compounds of formula (I) may also be effective in increasing the latency of HIV infection.

The compounds of formula (I) may also be useful in the treatment of diseases of excessive or unwanted platelet activation such as intermittent claudication, unstable angina, stroke, and acute coronary syndrome (e.g. occlusive vascular diseases).

The compounds of formula (I) may also be useful as a drug with diuretic action, or may be useful to treat overactive bladder syndrome.

The compounds of formula (I) may also be useful in the treatment of impotence or erectile dysfunction.

The compounds of formula (I) may also be useful in the treatment of bone disease characterised by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, calculosis, lithiasis (especially urolithiasis), gout and ankylosing spondylitis, tendinitis and bursitis.

The compounds of formula (I) may also be useful in bone remodelling and/or promoting bone generation and/or promoting fracture healing.

The compounds of formula (I) may also be useful for attenuating the hemodynamic side effects of NSAIDs and COX-2 inhibitors.

The compounds of formula (I) may also be useful in the treatment of cardiovascular diseases such as hypertension or myocardial ischemia; functional or organic venous insufficiency; varicose therapy; haemorrhoids; and shock states associated with a marked drop in arterial pressure (e.g. septic shock).

The compounds of formula (I) may also be useful in the treatment of neurodegenerative diseases such as dementia, particularly degenerative dementia (including senile dementia, Alzheimer's disease, Pick's disease, Huntingdon's chorea, Parkinson's disease and Creutzfeldt-Jakob disease, Amyotrophic lateral sclerosis (ALS), motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of formula (I) may also be useful in the treatment of neurological disorders and may be useful as neuroprotecting agents. The compounds of the invention may also be useful in the treatment of neurodegeneration following stroke, cardiac arrest, pulmonary bypass, traumatic brain injury, spinal cord injury or the like.

The compounds of formula (I) may also be useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of formula (I) may also be useful in the treatment of a kidney dysfunction (nephritis, particularly mesangial proliferative glomerulonephritis, nephritic syndrome), a liver dysfunction (hepatitis, cirrhosis) and gastrointestinal dysfunction (diarrhoea).

It is to be understood that as used herein any reference to treatment includes both treatment of established symptoms and prophylactic treatment.

According to a further embodiment the invention, there is provided a compound of formula (I) or a pharmaceutically acceptable derivative thereof for use in human or veterinary medicine.

According to another embodiment of the invention, there is provided a compound of formula (I) or a pharmaceutically acceptable derivative thereof for use in the treatment of a condition which is mediated by the action, or loss of action, of $PGE_2$ at $EP_4$ receptors.

According to a further embodiment of the invention, there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable derivative thereof.

According to a further embodiment of the invention there is provided a method of treating a human or animal subject suffering from a pain, or an inflammatory, immunological or bone disease, a neurodegenerative disease or a kidney dysfunction, which method comprises administering to said subject an effective amount of a compound of formula (I) or a pharmaceutically acceptable derivative thereof.

According to another embodiment of the invention, there is provided the use of a compound of formula (I) or a pharmaceutically acceptable derivative thereof for the manufacture of a medicament for the treatment of a condition which is mediated by the action of $PGE_2$ at $EP_4$ receptors.

According to another embodiment of the invention there is provided the use of a compound of formula (I) or a pharmaceutically acceptable derivative thereof for the manufacture of a medicament for the treatment or prevention of a condition such as a pain, or an inflammatory, immunological, bone, neurodegenerative or kidney disorder.

The compounds of formula (I) and their pharmaceutically acceptable derivatives are conveniently administered in the form of pharmaceutical compositions. Such compositions may conveniently be presented for use in conventional manner in admixture with one or more physiologically acceptable carriers or excipients.

Thus, in another aspect of the invention, there is provided a pharmaceutical composition comprising a compound of formula (I) or a pharmaceutically acceptable derivative thereof adapted for use in human or veterinary medicine.

While it is possible for the compounds of formula (I) or a pharmaceutically acceptable derivative thereof to be administered as the raw chemical, it is preferable to present it as a pharmaceutical formulation. The formulations of the present invention comprise the compounds of formula (I) or a pharmaceutically acceptable derivative thereof together with one or more acceptable carriers or diluents therefor and optionally other therapeutic ingredients. The carrier(s) must be "acceptable" in the sense of being compatible with the other ingredients of the formulation and not deleterious to the recipient thereof. Thus, in one embodiment the invention provides a pharmaceutical composition comprising a compound of formula (I) or a pharmaceutically acceptable derivative thereof and a pharmaceutically acceptable carrier or diluent therefor.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy (see for example methods disclosed in 'Remington—The Science and Practice of Pharmacy', 21$^{st}$ Edition, Lippincott, Williams & Wilkins, USA, 2005 and references therein). All methods include the step of bringing into association the compound of formula (I) or a pharmaceutically acceptable derivative thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds of formula (I) may also be formulated as depot preparations. Such long acting formulations may be administered by implantation (for example subcutaneously or intramuscularly) or by intramuscular injection. Thus, for example, the compounds of formula (I) may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

The compounds of formula (I) may be used in combination with other therapeutic agents, for example COX-2 inhibitors, such as celecoxib, rofecoxib, valdecoxib or parecoxib; 5-lipoxygenase inhibitors; analgesics such as paracetamol; NSAID's, such as diclofenac, indomethacin, nabumetone, naproxen or ibuprofen; leukotriene receptor antagonists; DMARD's such as methotrexate; sodium channel blockers, such as lamotrigine; N-type calcium channel antagonists; NMDA receptor modulators, such as glycine receptor antagonists; gabapentin, pregabalin and related compounds; tricyclic antidepressants such as amitriptyline; neurone stabilising antiepileptic drugs; mono-aminergic uptake inhibitors such as venlafaxine; opioid analgesics; local anaesthetics; $5HT_1$ agonists, such as triptans, for example sumatriptan, naratriptan, zolmitriptan, eletriptan, frovatriptan, almotriptan or rizatriptan; $EP_1$ receptor ligands; $EP_2$ receptor ligands; $EP_3$ receptor ligands; $EP_1$ antagonists; $EP_2$ antagonists and $EP_3$ antagonists; cannabanoid receptor agonists; VR1 antagonists. When the compounds are used in combination with other therapeutic agents, the compounds may be administered either sequentially or simultaneously by any convenient route.

The invention thus provides, in a further embodiment, a combination comprising a compound of formula (I) or a pharmaceutically acceptable derivative thereof together with a further therapeutic agent or agents. In one embodiment of the invention there is provided a combination comprising a compound of formula (I) or a pharmaceutically acceptable derivative thereof and paracetamol. In particular, the invention provides a combination comprising {4-[4,9-Bis(ethyloxy)-1-oxo-1,3-dihydro-2H-benzo[f]isoindol-2-yl]-2-fluorophenyl}acetic acid or a pharmaceutically acceptable derivative thereof and paracetamol.

In still a further embodiment of the invention there is provided a combination comprising an $EP_4$ receptor agonist or a pharmaceutically acceptable derivative thereof and paracetamol. Suitable $EP_4$ receptor agonists include those described herein, including compounds of formula (I) and those compounds described in WO02/064564, such as [4-(4,9-dipropoxy-1-oxo-1,3-dihydro-2H-benzo[f]isoindol-2-yl)phenyl] acetic acid and WO01/10426, such as [4-(4,9-diethoxy-1-oxo-1,3-dihydro-2H-benzo[f]isoindol-2-yl)phenyl]acetic acid.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. In particular there is provided a pharmaceutical composition comprising a compound of formula (I) or a pharmaceutically acceptable derivative thereof, paracetamol and a pharmaceutically acceptable carrier or diluent therefor. In another embodiment there is also provided a pharmaceutical composition comprising {4-[4,9-Bis(ethyloxy)-1-oxo-1,3-dihydro-2H-benzo[f]isoindol-2-yl]-2-fluorophenyl}acetic acid or a pharmaceutically acceptable derivative thereof, paracetamol and a pharmaceutically acceptable carrier or diluent therefor. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease, the dose of each compound may differ from that when the compound is used alone. Appropriate doses will be readily appreciated by those skilled in the art.

In one embodiment of the invention there is provided a method of treating a human or animal subject suffering from a condition which is mediated by the action, or by loss of action, of $PGE_2$ at $EP_4$ receptors which comprises administering to said subject an effective amount of a compound of formula (I) or a pharmaceutically acceptable derivative thereof and paracetamol.

In another embodiment of the invention there is provided a method of treating a human or animal subject suffering from a condition which is mediated by the action, or by loss of action, of $PGE_2$ at $EP_4$ receptors which comprises administering to said subject an effective amount of {4-[4,9-Bis(ethyloxy)-1-oxo-1,3-dihydro-2H-benzo[f]isoindol-2-yl]-2-fluorophenyl}acetic acid or a pharmaceutically acceptable derivative thereof and paracetamol.

A proposed daily dosage of compounds of formula (I) or their pharmaceutically acceptable salts for the treatment of man is from 0.001 to 30 mg/kg body weight per day and more particularly 0.1 to 3 mg/kg body weight per day, calculated as the free acid, which may be administered as a single or divided dose, for example one to four times per day. The dose range for adult human beings is generally from 0.1 to 1000 mg/day, such as from 10 to 800 mg/day, preferably 10 to 200 mg/day, calculated as the free acid.

A suitable daily dosage of paracetamol is up to 4000 mg per day. Suitable unit doses include 200, 400, 500 and 1000 mg, one, two, three or four times per day.

The precise amount of the compounds of formula (I) administered to a host, particularly a human patient, will be the responsibility of the attendant physician. However, the dose employed will depend on a number of factors including the age and sex of the patient, the precise condition being treated and its severity, the route of administration, and any possible combination therapy that may be being undertaken.

The present invention provides a process for preparing the compounds of formula (I) and pharmaceutically acceptable derivatives thereof.

Thus, in one embodiment of the invention there is provided a process for preparing a compound of formula (I) wherein, one of X and Y represents C=O and the other represents $CH_2$ and $R^1$, $R^2$, $R^3$, $R^4$, $R^5$ and $R^6$ are as hereinbefore defined in relation to formula (I), which process comprises reacting a compound of formula (II),

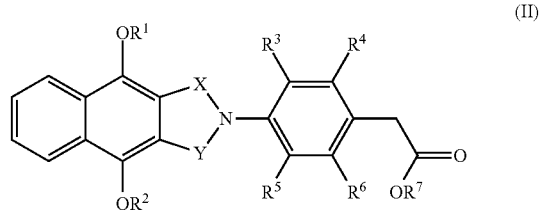

(II)

wherein, one of X and Y represents C=O and the other represents $CH_2$; $R^1$, $R^2$, $R^3$, $R^4$, $R^5$ and $R^6$ are as hereinbefore defined in relation to formula (I); and $R^7$ represents $C_{1-6}$ alkyl; with a suitable base, such as sodium hydroxide, and optionally thereafter forming a pharmaceutically acceptable derivative of the compound so formed, and/or converting one compound of formula (I) to another.

In one embodiment the above-mentioned reaction comprising a compound of formula (II) is performed in a suitable solvent, such as ethanol, under reflux.

In another embodiment of the invention there is provided a process for preparing a compound of formula (I), wherein X and Y represent C=O and $R^1$, $R^2$, $R^3$, $R^4$, $R^5$ and $R^6$ are as hereinbefore defined in relation to formula (I), which process comprises adding a compound of formula (III),

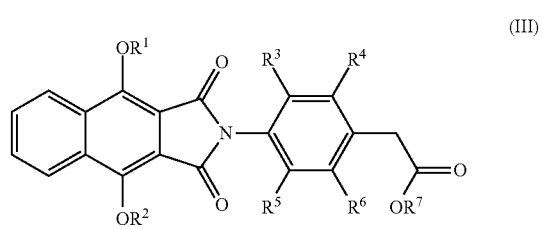

(III)

wherein, $R^1$, $R^2$, $R^3$, $R^4$, $R^5$ and $R^6$ are as hereinbefore defined in relation to formula (I); and $R^7$ represents $C_{1-6}$ alkyl; to a suitable acid or mixture of acids, such as glacial acetic acid in the presence of hydrochloric acid, and optionally thereafter forming a pharmaceutically acceptable derivative of the compound so formed, and/or converting one compound of formula (I) to another.

In one embodiment the above-mentioned reaction comprising a compound of formula (III) is performed at a temperature in the range from about 50 to 110° C., for a time period in the range from about 2 to 70 hours. In one embodiment, the molar ratio of glacial acetic acid to acid, such as hydrochloric acid, present in the reaction mixture is 1:1.

It will be appreciated that compounds of formula (I) wherein one of X and Y represents C=O and the other represents $CH_2$ and $R^1$, $R^2$, $R^3$ and $R^4$ are as hereinbefore defined in relation to formula (I), may also be prepared using the acid hydrolysis conditions outlined above.

Compounds of formula (II) and (III) may be prepared according to Scheme 1.
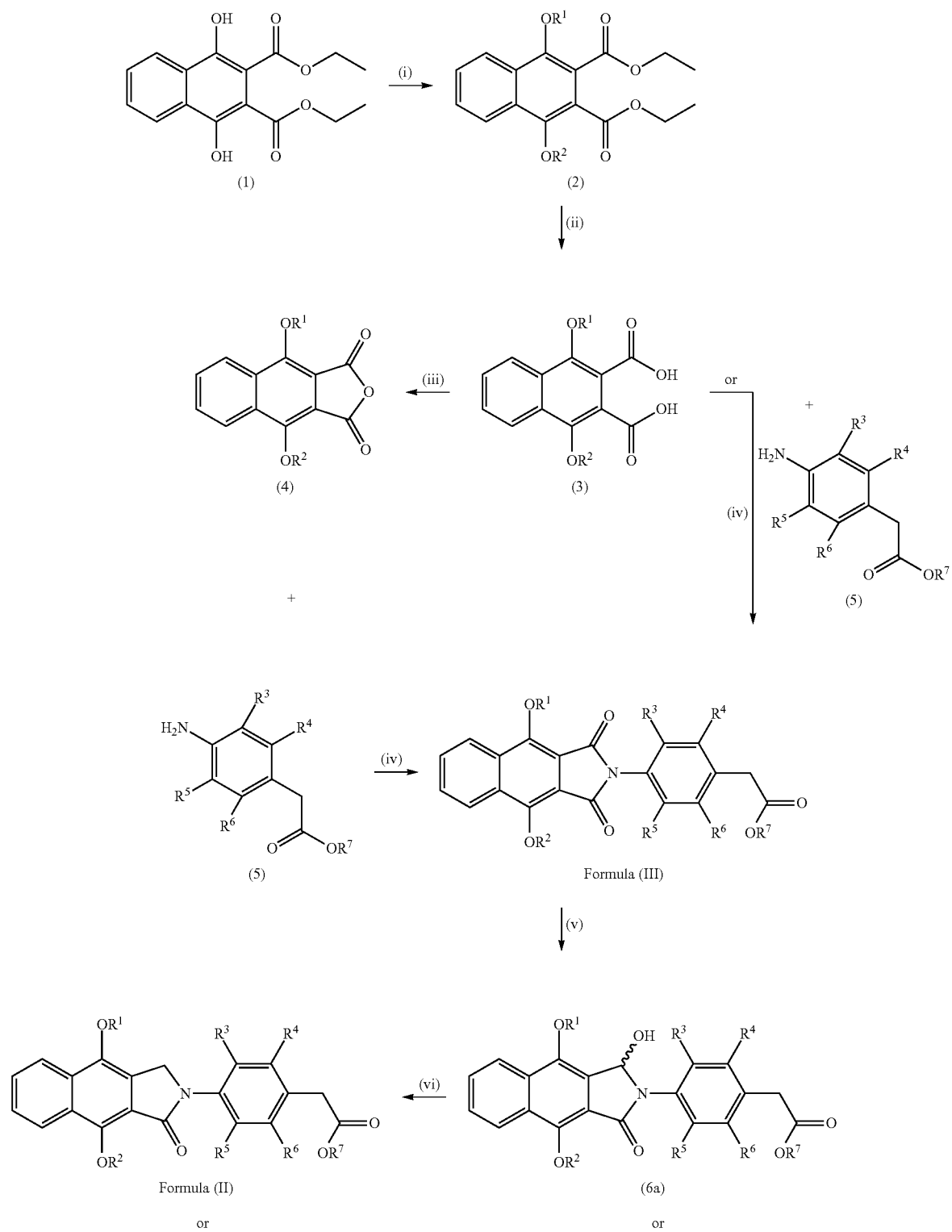

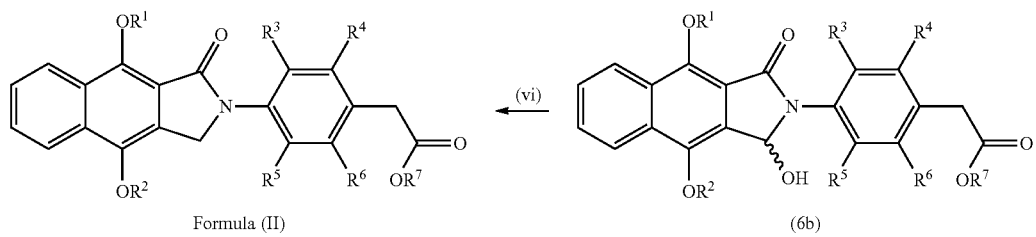

Formula (II)    (6b)

(i) R-Br or R-I, $K_2CO_3$, acetone;
(ii) NaOH/$H_2O$, EtOH;
(iii) $SOCl_2$, $CHCl_3$ or EtOH;
(iv) $CH_3CO_2H$, optionally DMAP;
(v) $NaBH_4$, MeOH/THF;
(vi) $Et_3SiH$, TFA or TFA/DCM or DCM; (where $R = R^1 = R^2$; and $R^1, R^2, R^3, R^4, R^5, R^6$, and $R^7$ are as defined in relation to formula (II)).

Compounds of formula (2) where $R^1 \neq R^2$ may be prepared by reacting the compound of formula (I) in a stepwise manner with an alkyl halide $R^1X$, followed by a second alkyl halide, $R^2X$, or vice versa, under the aforementioned conditions.

Compound (1) may be prepared from diethyl phthalate in accordance with the method disclosed in International Patent Application, Publication Number WO02/064564.

Compounds of formula (5) may be prepared according to Schemes 2, 3 and 4.

Scheme 2

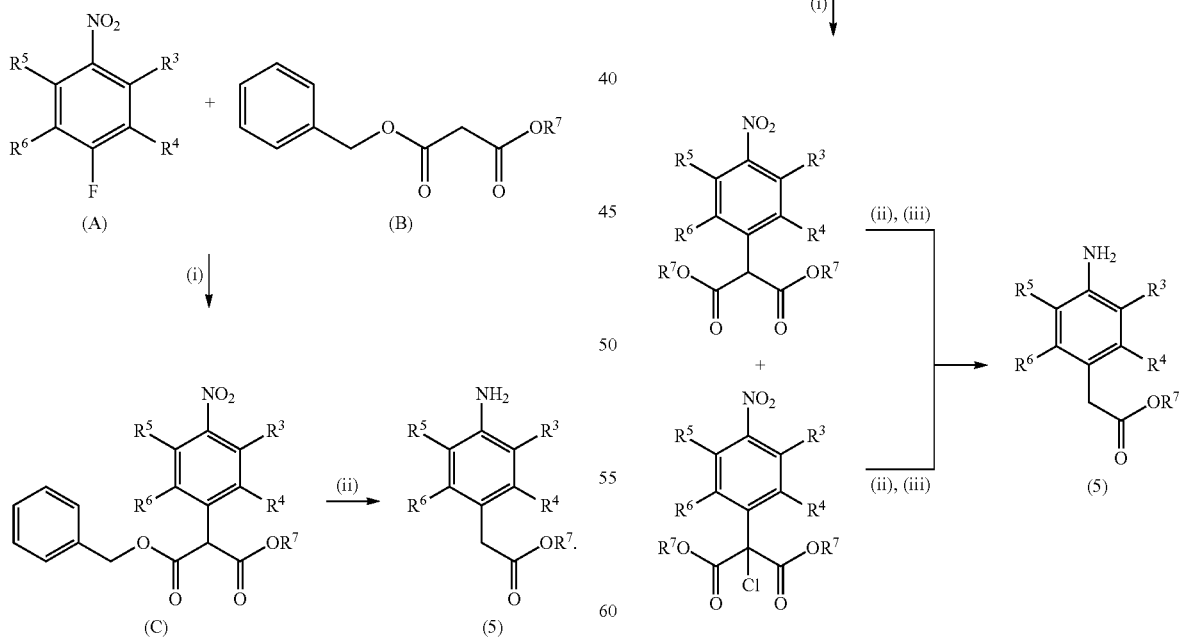

(i) NaH, dry DMF;
(ii) $NH_4CO_2H$, EtOH, Pd/C; (where $R^3, R^4, R^5, R^6$ and $R^7$ are as defined in relation to Formula (II)).

Scheme 3

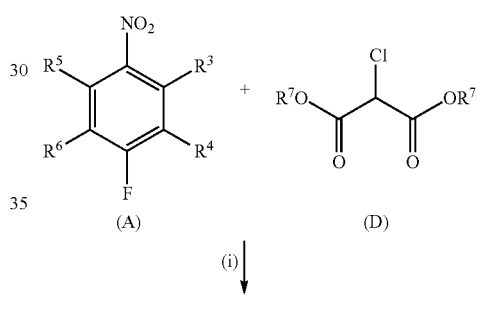

(i) NaOH, dry DMF;
(ii) $NH_4CO_2H$, EtOH, Pd/C;
(iii) NaOH, $H_2O$, EtOH (where $R^3, R^4, R^5, R^6$ and $R^7$ are as defined in relation to Formula (II)).

Scheme 4

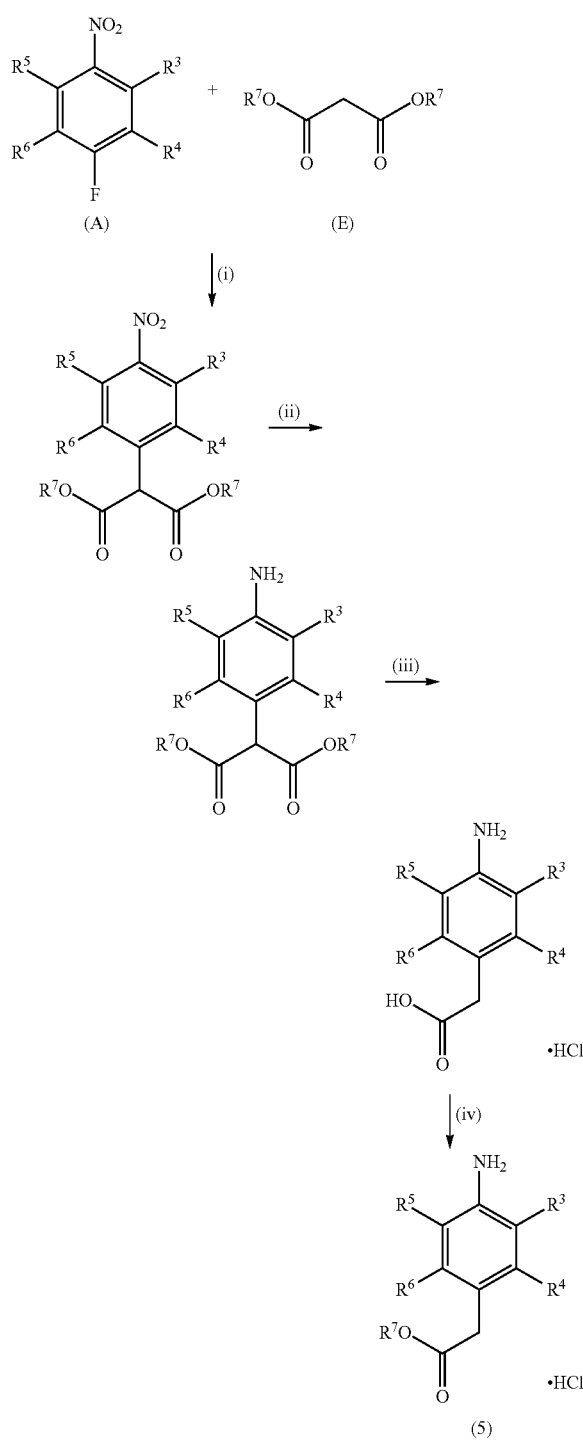

(i) Base (e.g. K$_2$CO$_3$). 50° C., dry DMF;
(ii) H$_2$, Pd/C;
(iii) HCl$_{(aq)}$; and
(iv) EtOH, HCl (where R$^3$, R$^4$, R$^5$, R$^6$ and R$^7$ are as defined in relation to Formula (II)).

Compounds of formula (A) are commercially available or may be prepared in accordance with methods known in the art (for example 2,4-difluoronitrobenzene and 3,4-difluoronitrobenzene may be purchased from Sigma-Aldrich Co. Ltd.).

Compounds of formula (B) are commercially available or may be prepared in accordance with methods known in the art (for example benzyl ethyl malonate may be purchased from Sigma-Aldrich Co. Ltd.).

Compounds of formula (D) are commercially available or may be prepared in accordance with methods known in the art (for example, diethylchloromalonate may be purchased from Sigma-Aldrich Co. Ltd).

Compounds of formula (E) are commercially available or may be prepared in accordance with methods known in the art (for example, diethylmalonate may be purchased from Sigma-Aldrich Co. Ltd).

In another embodiment of the invention there is provided a process for preparing a compound of formula (I) or a pharmaceutically acceptable derivative thereof, which process comprises reacting a compound of formula (3) or a compound of formula (4), as described in Scheme 1, with a compound of formula (IV),

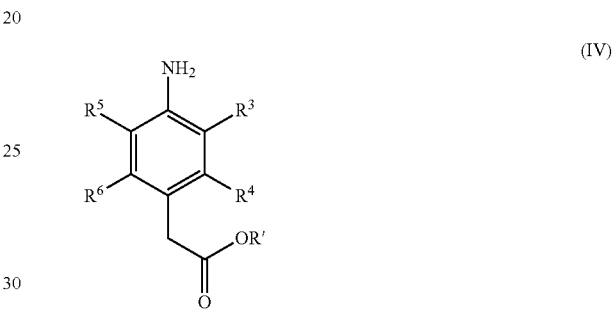

wherein R$^3$, R$^4$, R$^5$ and R$^6$ are as defined in relation to formula (I) and R' represents H or C$_{1-6}$ alkyl, and optionally thereafter forming a pharmaceutically acceptable derivative of the compound so formed, and/or converting one compound of formula (I) to another.

Compounds of formula (IV) where R' represents H may be prepared by the hydrolysis of compounds of formula (5).

The following Descriptions and Examples illustrate the preparation of the compounds of formula (I). Descriptions refer to intermediate compounds.

Abbreviations
DCM Dichloromethane
DMAP 4-(Dimethylamino)pyridine
DMF Dimethylformamide
DMSO Dimethylsulfoxide
EtOH Ethanol
EtOAc Ethyl acetate
HCl Hydrochloric acid
LC/MS Liquid chromatography/Mass spectroscopy
MeOH Methanol
MDAP Mass Directed Auto Preparation
NaOH Sodium hydroxide
TFA Trifluoroacetic acid
THF Tetrahydrofuran Analytical procedures
LC/MS
Column
Waters Atlantis (4.6 mm×50 mm). Stationary phase particle size, 3 µm.
Solvents
A: Aqueous solvent=Water+0.05% Formic Acid
B: Organic solvent=Acetonitrile+0.05% Formic Acid

19

Method

| Time/min | % B |
|---|---|
| 0 | 3 |
| 0.1 | 3 |
| 4 | 97 |
| 4.8 | 97 |
| 4.9 | 3 |
| 5.0 | 3 |

Flow rate, 3 ml/mins.
Injection volume, 5 μl.
Column temperature, 30° C.
UV detection range, 220 to 330 nm.
All retention times are measured in minutes.
As used herein 'CV' means column volumes.

NMR

$^1$H NMR spectra were recorded on a Bruker AVANCE 400 NMR spectrometer or a Bruker DPX250 NMR spectrometer. Chemical shifts are expressed in parts per million (ppm, δ units). Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Purification Techniques

Purification of the Examples may be carried out by conventional methods such as chromatography and/or recrystallisation using suitable solvents. Chromatographic methods include column chromatography, flash chromatography, HPLC (high performance liquid chromatography), SFC (supercritical fluid chromatography), and MDAP (mass directed autopreparation).

The term "Biotage" when used herein refers to commercially available pre-packed silica gel cartridges.

Mass Directed Auto Preparation (MDAP)
Column
Waters Atlantis: 19 mm×100 mm (small scale); and 30 mm×100 mm (large scale).
Stationary phase particle size, 5 μm.
Solvents
A: Aqueous solvent=Water+0.1% Formic Acid
B: Organic solvent=Acetonitrile+0.1% Formic Acid
Make up solvent=Methanol:Water 80:20
Needle rinse solvent=Methanol
Methods Five methods were used depending on the analytical retention time of the compound of interest:
(1) Large/Small Scale 1.0-1.5=5-30% B
(2) Large/Small Scale 1.5-2.2=15-55% B
(3) Large/Small Scale 2.2-2.9=30-85% B
(4) Large/Small Scale 2.9-3.6=50-99% B
Runtime, 13.5 minutes, comprising 10-minute gradient followed by a 3.5 minute column flush and re-equilibration step.
(5) Large/Small Scale 3.6-5.0=80-99% B
Runtime, 13.5 minutes, comprising 6-minute gradient followed by a 7.5 minute column flush and re-equilibration step.
Where indicated, 'shallow gradient' conditions were employed as follows:
Large 1.5 to 2.3 min=13-29% B
Large 1.9 to 2.3 min=25-41% B
Large 2.3 to 2.6 min=37-53% B
Large 2.6 to 3.1 min=49-65% B
Large 3.1 to 3.6 min=61-77% B

20

Runtime, 13.5 minutes, comprising 10-minute gradient followed by a 3.5 minute column flush and re-equilibration step.
Flow Rate
20 mls/min (Small Scale) or 40 mls/min (Large Scale).

Description 1a

Diethyl 1,4-bis(propyloxy)-2,3-naphthalenedicarboxylate

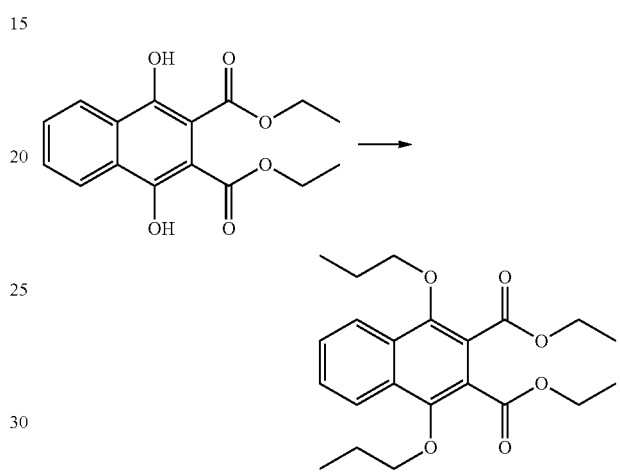

Diethyl 1,4-dihydroxy-2,3-naphthalenedicarboxylate* (11 g, 36.1 mmol) was dissolved in acetone (180 ml) and potassium carbonate (24.9 g, 180.5 mmol) added and stirred. 1-Bromopropane (13.1 ml, 144.4 mmol) was added and the reaction mixture was heated at reflux (60° C.) overnight under argon. The reaction was cooled to room temperature and the inorganic solid filtered off. The solvent was evaporated to give an orange brown oil. The residue was taken up in toluene and washed with 5% potassium hydroxide solution, brine and dried over magnesium sulphate. Solvent was removed under vacuum to give a brown oil which was purified by chromatography on silica gel eluting with, 10% ethyl acetate in hexane. The clean fractions were evaporated to give the title compound as yellow oil (11.45 g, 29.5 mmol).

LC/MS: Rt=3.87, [MH]+ 389

Description 1b

Diethyl 1,4-bis(ethyloxy)-2,3-naphthalenedicarboxylate

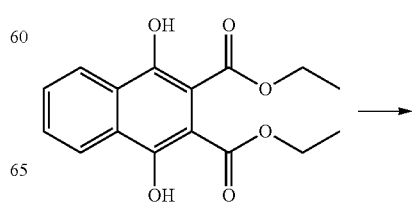

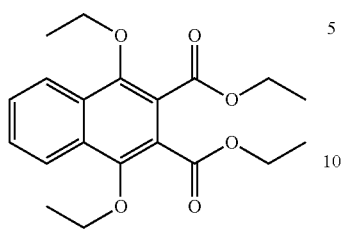

Diethyl 1,4-dihydroxy-2,3-naphthalenedicarboxylate* (25 g, 82.2 mmol) was dissolved in acetone (400 ml) and potassium carbonate (34 g, 246.5 mmol) was added. This was stirred for 20 minutes. Ethyl iodide (19.8 ml, 246.5 mmol) was added and heated to 60° C. for 7 hours. Cooled to room temperature and solid removed by filtration. Solvent was evaporated to give an orange oil which was partitioned between ethyl acetate and brine. Aqueous layer was extracted with ethyl acetate (×3) and combined organics washed with water and dried over MgSO$_4$. Evaporated to give a brown solid (~29 g). Crude material was purified by flash column chromatography eluting with 0-15% ethyl acetate in hexane over 30CV (hexane 2CV, 5% EtOAc/hexane 2CV, 10% EtOAc/hexane 4CV, 12% EtOAc/hexane 2CV, 15% EtOAc/hexane 20CV). Fractions evaporated to give pink solid. Triturated in cold hexane to give the title compound as a white solid (3 batches, total 24.83 g, 68.9 mmol).

LC/MS: Rt=3.52, [MH]$^+$ 287

*Diethyl 1,4-dihydroxy-2,3-naphthalenedicarboxylate may be prepared in accordance with the method disclosed in International Patent Application, Publication Number WO02/064564.

The following compound was prepared in a similar manner to diethyl 1,4-bis(propyloxy)-2,3-naphthalenedicarboxylate using the appropriate starting materials.

| Name | LC/MS |
|---|---|
| Diethyl 1,4-bis(1-methylethoxy)-2,3-naphthalenedicarboxylate | Rt = 3.63 [MH]$^+$ 389 |

Description 2a 1,4-Bis(propyloxy)-2,3-naphthalenedicarboxylic acid

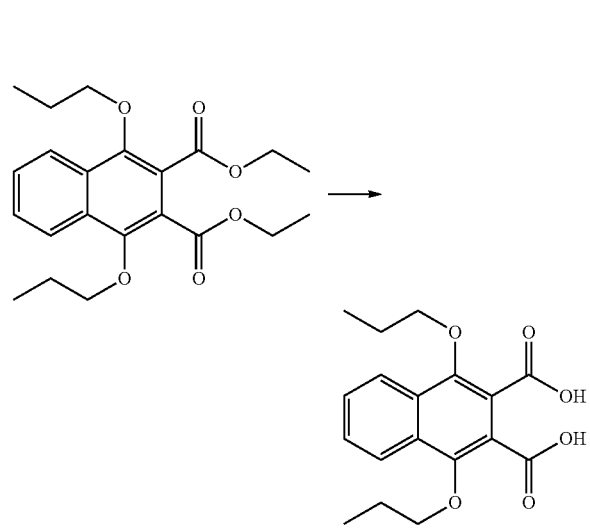

Diethyl 1,4-bis(propyloxy)-2,3-naphthalenedicarboxylate (11.45 g, 29.5 mmol) was dissolved in ethanol (70 ml) and treated with sodium hydroxide (3.54 g, 88.5 mmol) dissolved in water (15 ml). This was heated at 60° C. under argon for 4 hours. The reaction was confirmed to be complete by LC/MS and thin layer chromatography. The reaction mixture was cooled to room temperature and evaporated to a third of the volume. This was acidified to pH2 with hydrochloric acid (2N) and extracted with ethyl acetate (3×100 ml). Combined organics washed with water, brine and dried over magnesium sulphate. Solvent was evaporated to give the title compound as a yellow solid (8.91 g, 26.8 mmol).

LC/MS: Rt=2.74, [MH]$^+$ 333

Description 2b 1,4-Bis(ethyloxy)-2,3-naphthalenedicarboxylic acid

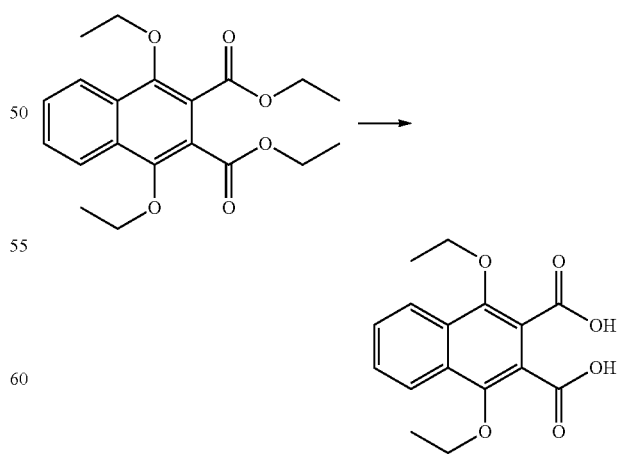

Diethyl 1,4-bis(ethyloxy)-2,3-naphthalenedicarboxylate (24.8 g, 68.8 mmol) was suspended in ethanol (200 ml) and treated with sodium hydroxide (8.3 g, 206.4 mmol) dissolved in 200 ml of water. A further 50 ml of ethanol added to aid stirring. Heated to reflux, 100° C. All in solution on heating. Refluxed for 8 hours. Cooled to room temperature and stood overnight. Solvent was evaporated to almost dryness. Water was added and stirred in an ice bath. Acidified with 2M HCl solution (~150 ml). The white precipitate was filtered, washed with water and dried in a vacuum oven to give the title compound as a white solid (18.77 g, 61.7 mmol).

LC/MS: Rt=2.34, [MH]⁺ 305

The following compound was prepared in a similar manner to 1,4-bis(propyloxy)-2,3-naphthalenedicarboxylic acid using the appropriate starting materials.

| Name | LC/MS |
|---|---|
| 1,4-Bis(1-methylethoxy)-2,3-naphthalenedicarboxylic acid | Rt = 2.50 [MH]⁻ 331 |

Description 3a 4,9-Bis(propyloxy)naphtho[2,3-c]furan-1,3-dione

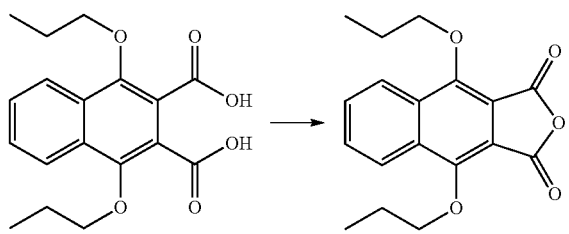

1,4-Bis(propyloxy)-2,3-naphthalenedicarboxylic acid (8.91 g, 26.8 mmol) was suspended in chloroform (80 ml) and thionyl chloride (20.5 ml, 281.4 mmol) was added dropwise whilst monitoring the temperature (no significant change). The reaction was heated at 65° C. for 2.5 hours. The reaction mixture was cooled to room temperature and concentrated in vacuo. The yellow/brown solid was azeotroped with chloroform (×3) to afford the title compound as a beige solid (8.74 g, 27.8 mmol).

LC/MS: Rt=3.77, [MH]⁺ 315

Description 3b 4,9-Bis(ethyloxy)naphtho[2,3-c]furan-1,3-dione

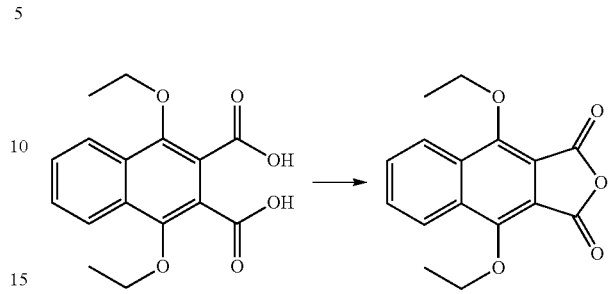

1,4-Bis(ethyloxy)-2,3-naphthalenedicarboxylic acid (10.3 g, 33.8 mmol) was added to a three neck flask and chloroform (80 ml) added and stirred. Thionyl chloride (49.2 ml, 355.4 mmol) in a dropping funnel was added dropwise over 25 minutes whilst monitoring temperature (no change). The reaction was heated at relfux (65° C.) overnight. LC/MS indicated no starting material remained. Reaction mixture was cooled to room temperature and solvent evaporated. The product was azeotroped with chloroform (×2) to remove the remaining traces of thionyl chloride to give the title compound as*a pale yellow solid (9.86 g).

LC/MS: Rt=3.48, [MH]⁺ 287

The following compound was prepared in a similar manner to 4,9-bis(propyloxy)naphtho[2,3-c]furan-1,3-dione using the appropriate starting materials.

| Name | LC/MS |
|---|---|
| 4,9-Bis(1-methylethoxy)naphtho[2,3-c]furan-1,3-dione | Rt = 3.6 [MH]⁺ 315 |

Description 4

Ethyl phenylmethyl (2-fluoro-4-nitrophenyl)propanedioate

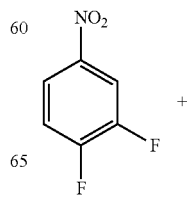

+

-continued

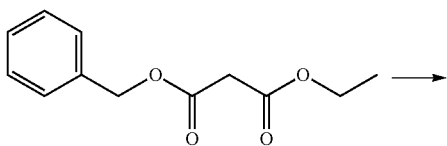

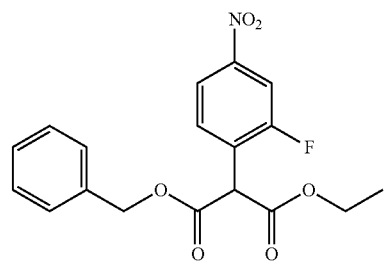

Benzyl ethyl malonate (2.9 g, 12.6 mmol) in dry DMF (20 ml) was cooled in an ice bath and the temperature monitored whilst sodium hydride (504 mg, 12.6 mmol) was added portionwise. This was stirred at room temperature for 10 minutes until $H_2$ evolution ceased. 3,4-Difluoronitrobenzene (2 g, 12.6 mmol) was added under an argon atmosphere and gave a dark red colour change. The reaction mixture was heated at 100° C. for 20 hours under argon. Thin layer chromatography (20% ethyl acetate in hexane) showed completion of the reaction. The reaction mixture was cooled to room temperature and partitioned between 2N Hydrochloric acid (75 ml) and ethyl acetate (75 ml). The aqueous layer was extracted with ethyl acetate (2×75 ml) and the combined organic fractions were evaporated to a yellow oil. Purification by chromatography on silica gel eluting with 0-20% ethyl acetate in hexane gave the title compound as a yellow oil (3.86 g, 10.6 mmol).

LC/MS: Rt=3.40, [MH]$^+$ 362

The following compound was prepared in a similar manner to ethyl phenylmethyl (2-fluoro-4-nitrophenyl)propanedioate using the appropriate starting materials.

| Name | LC/MS |
|---|---|
| Ethyl phenylmethyl (3-fluoro-4-nitrophenyl)propanedioate | Rt = 3.30 [MH]$^+$ 362 |

Description 5

Ethyl (4-amino-2-fluorophenyl)acetate

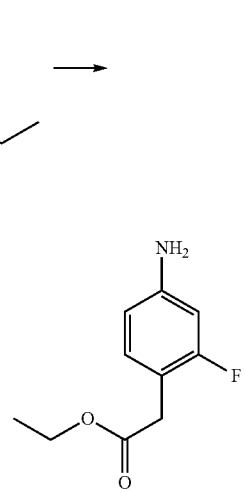

Ethyl phenylmethyl (2-fluoro-4-nitrophenyl)propanedioate (3.86 g, 10.6 mmol) dissolved in ethanol (50 ml), was treated with ammonium formate (6.7 g, 10.6 mmol) under argon. Palladium on carbon 10% paste (380 mg) was added and the reaction was stirred under reflux for 3 hours (60° C.). The reaction was cooled to room temperature and the catalyst removed by filtration through celite. Solvent was removed to give a brown oil. The crude material was purified by chromatography on silica gel eluting with 0-50% ethyl acetate in hexane (1:1) over 45 minutes. Fractions were evaporated to give the title compound as a yellow oil (1.26 g, 6.4 mmol).

LC/MS: Rt=2.10, [MH]$^+$ 198

The following compound was prepared in a similar manner to ethyl (4-amino-2-fluorophenyl)acetate, using the appropriate starting materials.

| Name | LC/MS |
|---|---|
| Ethyl (4-amino-3-fluorophenyl)acetate | Rt = 2.20 [MH]$^+$ 198 |

Description 6

Diethyl chloro(3-fluoro-4-nitrophenyl)propanedioate and Diethyl (3-fluoro-4-nitrophenyl)propanedioate

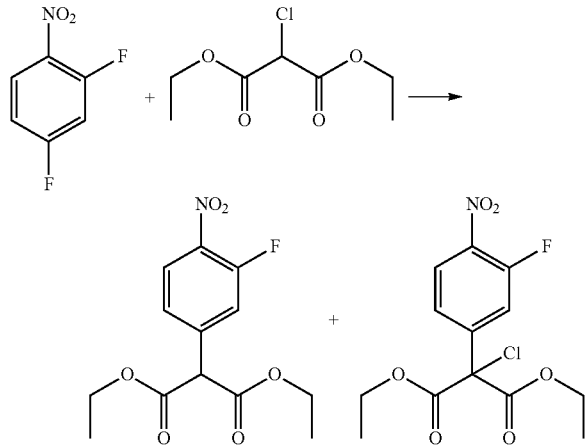

2,4-Difluoronitrobenzene (31.5 ml, 287 mmol) and diethylchloromalonate (46.4 ml, 287 mmol) dissolved in dry DMF (300 ml) was cooled in an ice bath. Crushed sodium hydroxide was added portionwise over 20 minutes. Reaction mixture was stirred at room temperature overnight. Reaction again cooled in an ice bath and acidified with 2N HCl (~400 ml). Extracted with ethyl acetate (2×400 ml, 1×200 ml), organics washed with water and dried over MgSO$_4$. Evaporated to give an orange oil (~89 g). Material was loaded onto 1.5 Kg Si cartridge and purified on CombiFlash® Companion™ XL eluting 0-20% ethyl acetate in hexane over 10 column volumes. Fractions were evaporated to yield diethyl chloro(3-fluoro-4-nitrophenyl)propanedioate as a yellow oil (9.09 g), diethyl (3-fluoro-4-nitrophenyl)propanedioate as a yellow oil (24.7 g,) and a mixture of the 2 as a yellow oil which crystallised on standing (1.7 g,).

Diethyl chloro(3-fluoro-4-nitrophenyl)propanedioate
  LCMS rt=3.18;
  $^1$H NMR (CDCl$_3$) δ ppm: 1.32 (6H, t, J=7.8 Hz), 4.35 (4H, m), 7.64 (1H, dd, J=11.9, 2.1 Hz), 7.56 (1H, ddd, J=8.9, 2.1, 1.1 Hz), 8.08 (1H, dd, J=8.7, 7.6 Hz).

Diethyl (3-fluoro-4-nitrophenyl)propanedioate
  LCMS rt=2.96, MH$^+$=300;
  $^1$H NMR (CDCl$_3$) δ ppm: 1.29 (6H, t, J=7.1 Hz), 4.25 (4H, m), 4.67 (1H, s), 7.45 (1H, dd, J=11.5, 1.8 Hz), 7.35 (1H, ddd, J=8.6, 1.5, 0.8 Hz), 8.06 (1H, dd, J=8.4, 7.9 Hz).

Description 7

Diethyl (4-amino-3-fluorophenyl)propanedioate

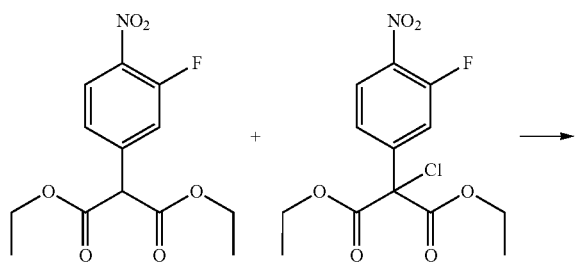

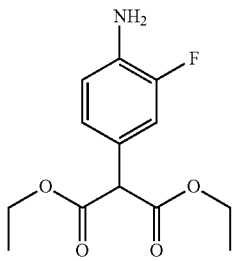

A mixture of diethyl chloro(3-fluoro-4-nitrophenyl)propanedioate and diethyl (3-fluoro-4-nitrophenyl)propanedioate (1.7 g, ~5.7 mmol) suspended in ethanol was treated with 5-10 ml ethyl acetate until in solution. This was treated with 10% Pd/C (wet paste) (170 mg) under argon and then ammonium formate (1.8 g, 5 eq) added. Stirred for 1 hour at reflux under argon. Cooled to room temperature and Pd removed by filtration through celite, under argon. Evaporated to a brown oil ~1.7 g. Purified by flash chromatography, 40+™M Si cartridge, eluting 5-40% ethyl acetate in hexane over 10 column volumes. Fraction evaporated to give the title compound as a yellow oil (722 mg).

LCMS rt=2.65, MH$^+$=270.

Description 8

Ethyl (4-amino-3-fluorophenyl)acetate

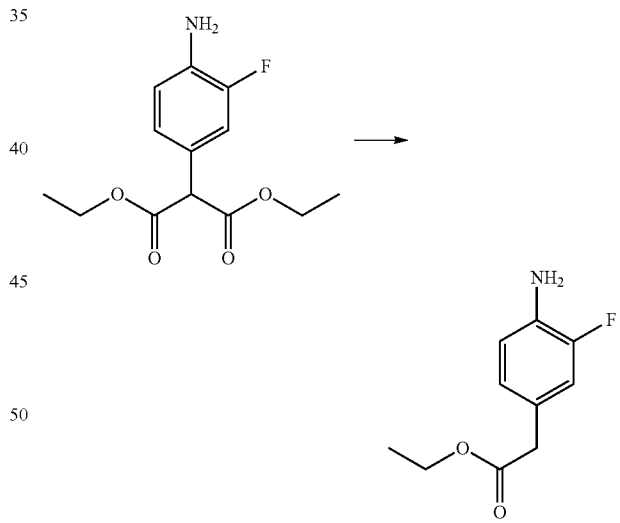

Diethyl (4-amino-3-fluorophenyl)propanedioate (11.85 g, 44.1 mmol) was dissolved in ethanol (80 ml) and treated with NaOH (2.6 g, 1.5 eq) dissolved in 18 ml of water to give a pink solution. This was heated to 90° C. for 1 hour until complete. Heating continued for 1 further hour, and then cooled to room temperature. Solvent evaporated and acidified with 2N HCl. Extracted with ethyl acetate (3×100 ml). Organics washed with brine and dried over MgSO$_4$. Evaporated to give the title compound as a yellow oil which crystallised slowly on standing (6.6 g).

LCMS rt=2.28, MH$^+$=198.

Description 9

Ethyl {4-[4,9-bis(ethyloxy)-1,3-dioxo-1,3-dihydro-2H-benzo[f]isoindol-2-yl]-3-fluorophenyl}acetate

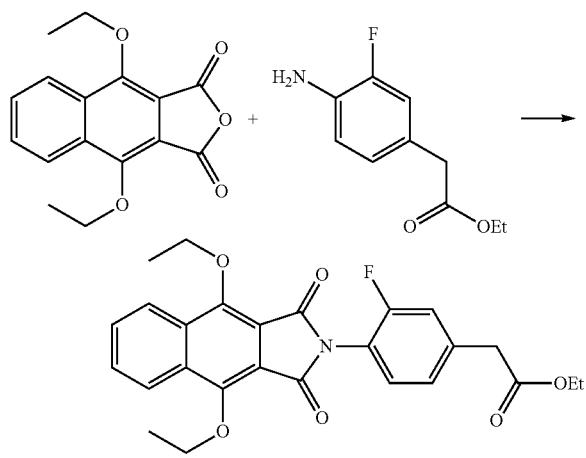

4,9-Bis(ethyloxy)naphtho[2,3-c]furan-1,3-dione (0.100 g, 0.35 mmol) in acetic acid (5 ml) was treated with DMAP (0.013 g, 0.11 mmol) then ethyl (4-amino-3-fluorophenyl)acetate (0.138 g, 0.70 mmol) and heated to reflux (120° C.) under argon overnight. The reaction mixture was cooled to room temperature and the solvent evaporated to afford a brown/orange oil which was diluted in DCM and washed with saturated NaHCO$_3$ and then 2N HCl. The organics were dried over MgSO$_4$ and evaporated to a brown oil which was purified by chromatography on silica gel eluting with ethyl acetate (0-20%) in hexane over 30 minutes. The evaporated fractions were triturated with hexane to give the title compound as a solid (0.110 g, 0.24 mmol, 69%).

LC/MS: Rt=3.74, [MH]$^+$ 466

The following compounds were prepared in a similar manner to ethyl {4-[4,9-bis(ethyloxy)-1,3-dioxo-1,3-dihydro-2H-benzo[f]isoindol-2-yl]-3-fluorophenyl}acetate, using the appropriate starting materials.

| | Name | LC/MS |
|---|---|---|
| | Ethyl {4-[1,3-dioxo-4,9-bis(propyloxy)-1,3-dihydro-2H-benzo[f]isoindol-2-yl]-2-fluorophenyl}acetate | Rt = 4.13 [MH]$^+$ 494 |
| | Ethyl {4-[1,3-dioxo-4,9-bis(propyloxy)-1,3-dihydro-2H-benzo[f]isoindol-2-yl]-3-fluorophenyl}acetate | Rt = 4.05 [MH]$^+$ 494 |
| | Ethyl (4-{4,9-bis(1-methylethoxy)-1,3-dioxo-1,3-dihydro-2H-benzo[f]isoindol-2-yl}-2-fluorophenyl)acetate | Rt = 4.01 [MH]$^+$ 494 |

| | Name | LC/MS |
|---|---|---|
| 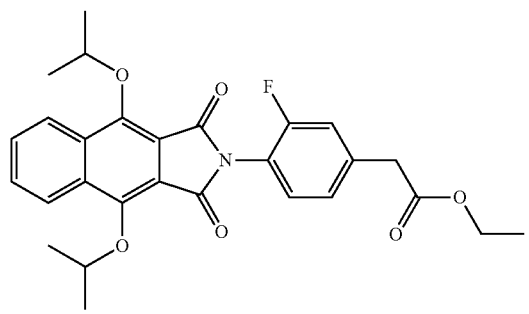 | Ethyl (4-{4,9-bis(1-methylethoxy)-1,3-dioxo-1,3-dihydro-2H-benzo[f]isoindol-2-yl}-3-fluorophenyl)acetate | Rt = 3.92 [MH]⁺ 494 |

Description 10

Ethyl {4-[4,9-bis(ethyloxy)-1,3-dioxo-1,3-dihydro-2H-benzo[f]isoindol-2-yl]-2-fluorophenyl}acetate

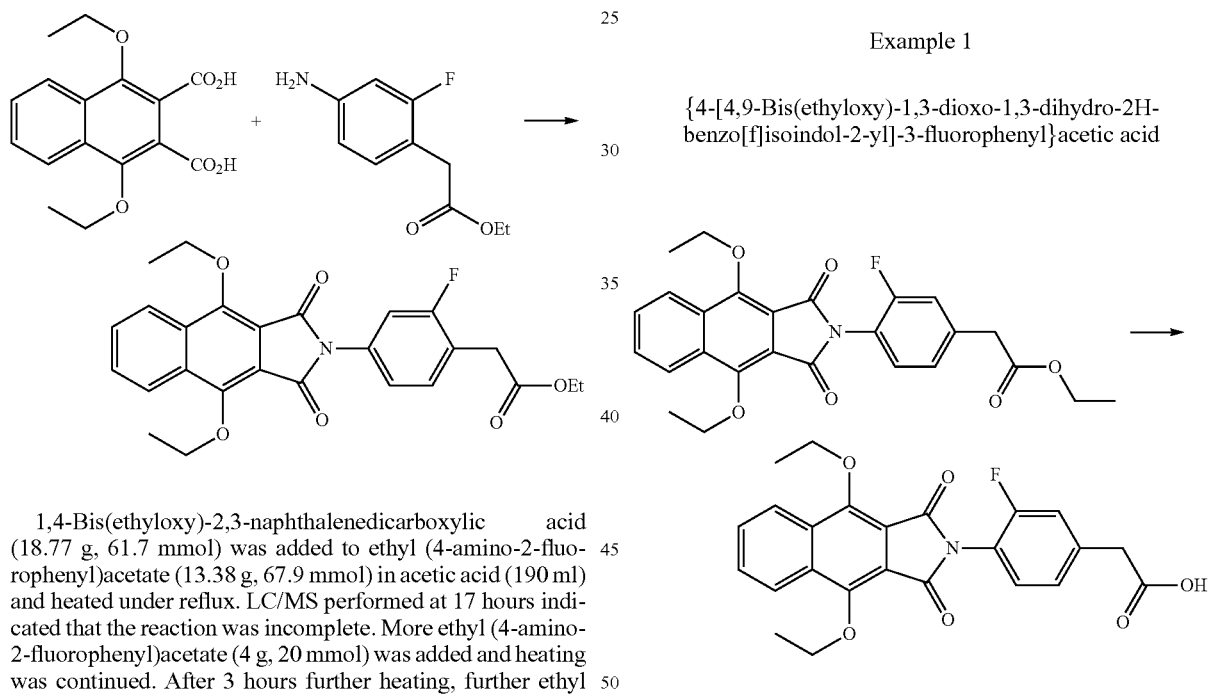

1,4-Bis(ethyloxy)-2,3-naphthalenedicarboxylic acid (18.77 g, 61.7 mmol) was added to ethyl (4-amino-2-fluorophenyl)acetate (13.38 g, 67.9 mmol) in acetic acid (190 ml) and heated under reflux. LC/MS performed at 17 hours indicated that the reaction was incomplete. More ethyl (4-amino-2-fluorophenyl)acetate (4 g, 20 mmol) was added and heating was continued. After 3 hours further heating, further ethyl (4-amino-2-fluorophenyl)acetate (3 g, 15 mmol) was added and heating was continued. After a further 2 hours of heating, more ethyl (4-amino-2-fluorophenyl)acetate (3 g, 15 mmol) was added and heating continued for a further 6 hours. The reaction mixture was then cooled and the product crystallised out of solution. Diluted with water (200 ml) and further precipitate formed. Filtered and the solid washed with further acetic acid (500 ml) to remove as much colour as possible, then washed with water (500 ml). The solid was dried in a vacuum oven overnight to give a light brown solid (12.01 g). The water solution was again filtered and the solid washed with further acetic acid and water, and dried to give a light brown solid (1.4 g). The acid solution from above was again filtered and the solid washed with further acetic acid and water, and dried to give a light brown solid (6.12 g). All the acid filtrates were concentrated in vacuo (~250 ml) and cooled. The solid that crystallised was filtered, washed with further acetic acid (50 ml), water, and dried to give a white solid (2.19 g). Further solid crystallised in the filtrate which was filtered, washed with further acetic acid (50 ml), water, and dried to give a brown solid (3.76 g, ~60% purity=2.27 g product). Total yield of title compound 24 g.

LC/MS: Rt=3.81, [MH]⁺ 466

Example 1

{4-[4,9-Bis(ethyloxy)-1,3-dioxo-1,3-dihydro-2H-benzo[f]isoindol-2-yl]-3-fluorophenyl}acetic acid Ethyl {4-[4,9-bis(ethyloxy)-1,3-dioxo-1,3-dihydro-2H-benzo[f]isoindol-2-yl]-3-fluorophenyl}acetate (0.050 g, 0.11 mmol) was dissolved in glacial acetic acid (2 ml) and 2N hydrochloric acid (2 ml) added which caused precipitation. The reaction mixture was heated to 100° C. under argon (the precipitate went back into solution) for 2 hours. The reaction mixture was cooled to room temperature and water added with stirring for 5 minutes. A solid precipitate formed which was filtered, washed with water, and collected to give the title compound as a yellow solid. The product was dried overnight in a vacuum oven (0.024 g, 0.05 mmol).

LC/MS: Rt=3.27, [MH]⁺ 438

The following compounds were prepared in a similar manner to {4-[4,9-bis(ethyloxy)-1,3-dioxo-1,3-dihydro-2H-benzo[f]isoindol-2-yl]-3-fluorophenyl}acetic acid using the appropriate starting materials.

| Example | | Name | LC/MS |
|---|---|---|---|
| Example 2 | | {4-[1,3-Dioxo-4,9-bis(propyloxy)-1,3-dihydro-2H-benzo[f]isoindol-2-yl]-3-fluorophenyl}acetic acid | Rt = 3.63 [MH]$^+$ 466 |
| Example 3 | | (4-{4,9-Bis(1-methylethoxy)-1,3-dioxo-1,3-dihydro-2H-benzo[f]isoindol-2-yl}-3-fluorophenyl)acetic acid | Rt = 3.41 [MH]$^+$ 466 |

Description 11

Ethyl {4-[4,9-bis(ethyloxy)-1-hydroxy-3-oxo-1,3-dihydro-2H-benzo[f]isoindol-2-yl]-3-fluorophenyl}acetate

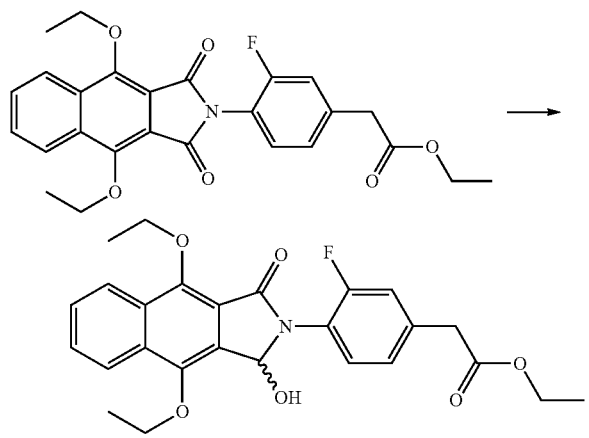

Ethyl {4-[4,9-bis(ethyloxy)-1,3-dioxo-1,3-dihydro-2H-benzo[f]isoindol-2-yl]-3-fluorophenyl}acetate (0.112 g, 0.24 mmol) was suspended in methanol (2 ml) and tetrahydrofuran (3 ml) added to dissolve the reactant. The reaction mixture was cooled to 0° C. in an ice bath and sodium borohydride (0.027 g, 0.72 mmol) added portionwise. Stirred under argon for 2-3 hours at 0° C. Further sodium borohydride was added to the reaction to push it to completion. The reaction mixture was evaporated to a solid and partitioned between EtOAc and ammonium chloride (saturated). The aqueous layer was extracted with EtOAc (×2) and the combined organics washed with brine and dried over MgSO$_4$. Solvent was evaporated to give the title product as a gummy residue, which was triturated with hexane to afford a solid (0.111 g, 0.23 mmol).
LC/MS: Rt=3.29, [MH]$^+$ 468

The following compounds were prepared in a similar manner to ethyl {-4-[4,9-bis(ethyloxy)-1-hydroxy-3-oxo-1,3-dihydro-2H-benzo[f]isoindol-2-yl]-3-fluorophenyl}acetate using the appropriate starting materials.

| | Name | LC/MS |
|---|---|---|
| | Ethyl {2-fluoro-4-[1-hydroxy-3-oxo-4,9-bis(propyloxy)-1,3-dihydro-2H-benzo[f]isoindol-2-yl]phenyl}acetate | Rt = 3.84 [MH]$^+$ 496 |

| Name | LC/MS |
|---|---|
| Ethyl (2-fluoro-4-{1-hydroxy-4,9-bis(1-methylethoxy)-3-oxo-1,3-dihydro-2H-benzo[f]isoindol-2-yl}phenyl)acetate | Rt = 3.68 [MH]$^+$ 496 |
| Ethyl {3-fluoro-4-[1-hydroxy-3-oxo-4,9-bis(propyloxy)-1,3-dihydro-2H-benzo[f]isoindol-2-yl]phenyl}acetate | Rt = 3.64 [MH]$^+$ 496 |
| Ethyl (3-fluoro-4-{1-hydroxy-4,9-bis(1-methylethoxy)-3-oxo-1,3-dihydro-2H-benzo[f]isoindol-2-yl}phenyl)acetate | Rt = 3.52 [MH]$^+$ 496 |

Description 12

Ethyl {4-[4,9-bis(ethyloxy)-1-hydroxy-3-oxo-1,3-dihydro-2H-benzo[f]isoindol-2-yl]-2-fluorophenyl}acetate

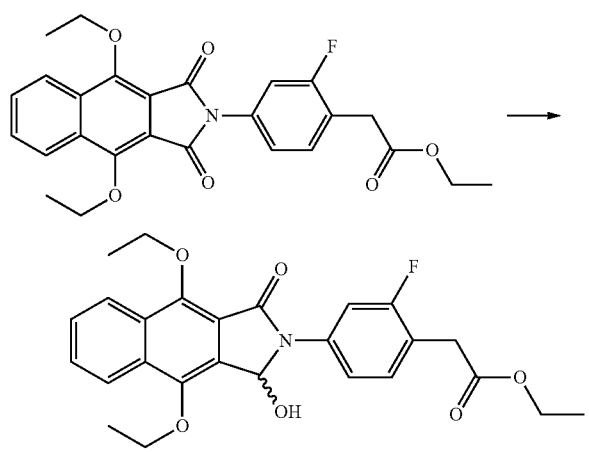

Ethyl {4-[4,9-bis(ethyloxy)-1,3-dioxo-1,3-dihydro-2H-benzo[f]isoindol-2-yl]-2-fluorophenyl}acetate (24 g, 51.6 mmol) was suspended in methanol (75 ml) and tetrahydrofuran (200 ml) and cooled to 5° C. in an ice bath. Some solid did not go into solution. Sodium borohydride (2 g, 51.6 mmol) was added portionwise over 2 minutes (effervescence). Undissolved solid slowly went into solution and the colour lightened from dark brown to light brown. LC/MS after 5 minutes and 30 minutes indicated that the reaction had not proceeded to completion. Therefore, after 30 minutes, more sodium borohydride (1 g, 26.3 mmol) was added in one portion (effervescence). LC/MS after a further 30 minutes showed no starting material remaining. The mixture was concentrated in vacuo to give a brown oil that was partitioned between ethyl acetate (300 ml) and water (500 ml). The aqueous layer was further extracted with ethyl acetate (2×100 ml). Combined organics were washed with brine, dried over magnesium sulphate and concentrated to give the title compound as a brown solid (26 g).

LC/MS: Rt=3.47, [MH]$^+$ 468.

Description 13

Ethyl {4-[4,9-bis(ethyloxy)-1-oxo-1,3-dihydro-2H-benzo[f]isoindol-2-yl]-3-fluorophenyl}acetate

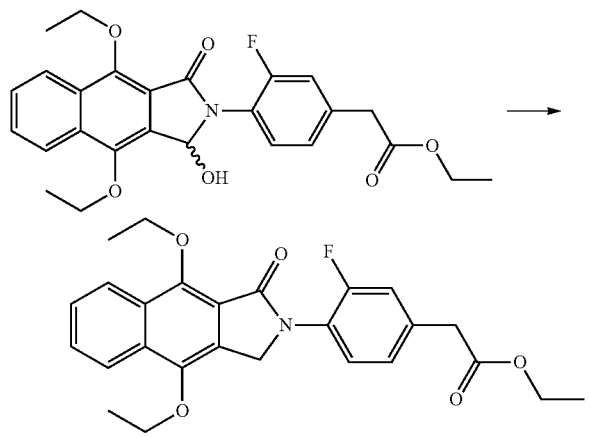

Ethyl {4-[4,9-bis(ethyloxy)-1-hydroxy-3-oxo-1,3-dihydro-2H-benzo[f]isoindol-2-yl]-3-fluorophenyl}acetate (0.111 g, 0.24 mmol) was dissolved in trifluoroacetic acid (5 ml) [instant orange solution] and cooled in an ice bath to 0° C. Treated drop wise with triethylsilane (0.06 ml, 0.36 mmol) and stirred at 0° C. under argon. The reaction was complete after 30-60 minutes. Trifluoroacetic acid was evaporated to afford a yellow oil which was purified directly by chromatography on silica gel eluting with ethyl acetate (0-20%) in hexane over 30 minutes. Fractions were evaporated to a colourless gum, which on trituration with hexane gave a white solid (0.072 g, 0.16 mmol).

LC/MS: Rt=3.65, [MH]$^+$ 452.

The following compounds were prepared in a similar manner to ethyl {4-[4,9-bis(ethyloxy)-1-oxo-1,3-dihydro-2H-benzo[f]isoindol-2-yl]-3-fluorophenyl}acetate using the appropriate starting materials.

| | Name | LC/MS |
|---|---|---|
| | Ethyl {2-fluoro-4-[1-oxo-4,9-bis(propyloxy)-1,3-dihydro-2H-benzo[f]isoindol-2-yl]phenyl}acetate | Rt = 4.10 [MH]$^+$ 480 |
| | Ethyl (4-{4,9-bis(1-methylethoxy)-1-oxo-1,3-dihydro-2H-benzo[f]isoindol-2-yl}-2-fluorophenyl)acetate | Rt = 4.10 [MH]$^+$ 480 |
| | Ethyl {3-fluoro-4-[1-oxo-4,9-bis(propyloxy)-1,3-dihydro-2H-benzo[f]isoindol-2-yl]phenyl}acetate | Rt = 3.99 [MH]$^+$ 480 |

| Name | LC/MS |
|---|---|
| Ethyl (4-{4,9-bis(1-methylethoxy)-1-oxo-1,3-dihydro-2H-benzo[f]isoindol-2-yl}-3-fluorophenyl)acetate | Rt = 3.87 [MH]+ 480 |

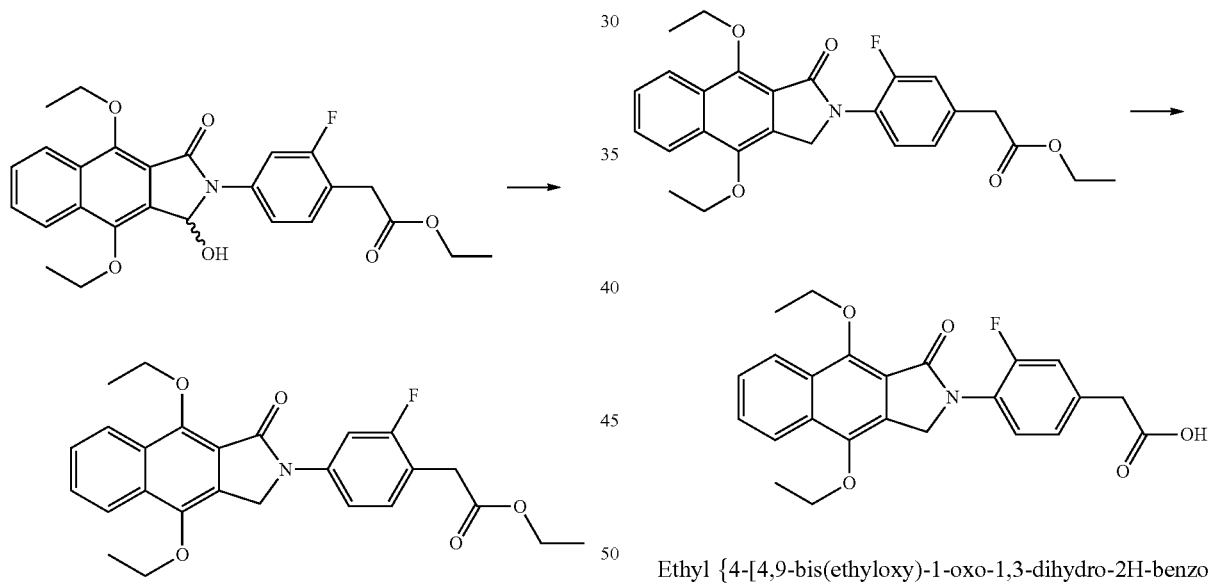

Description 14

Ethyl {4-[4,9-bis(ethyloxy)-1-oxo-1,3-dihydro-2H-benzo[f]isoindol-2-yl]-2-fluorophenyl}acetate Ethyl {4-[4,9-bis(ethyloxy)-1-hydroxy-3-oxo-1,3-dihydro-2H-benzo[f]isoindol-2-yl]-2-fluorophenyl}acetate (approx. 51.6 mmol) was dissolved in CH$_2$Cl$_2$ (50 ml) and cooled to 0° C. and TFA (50 ml) added. Triethylsilane (12.3 ml, 77 mmol) was added in one portion to give a brown solution. The solution was concentrated in vacuo to give a tan solid. This was recrystallised from hot isopropanol (550 ml), cooled, filtered, washed with isopropanol, and dried in a vacuum oven to give the title compound as off white crystals (20.2 g).

LC/MS: Rt=3.89, [MH]+ 452

Example 4

{4-[4,9-Bis(ethyloxy)-1-oxo-1,3-dihydro-2H-benzo[f]isoindol-2-yl]-3-fluorophenyl}acetic acid Ethyl {4-[4,9-bis(ethyloxy)-1-oxo-1,3-dihydro-2H-benzo[f]isoindol-2-yl]-3-fluorophenyl}acetate (0.072 g, 0.16 mmol) was suspended in ethanol (2 ml) and treated with 2N sodium hydroxide (6 ml). Heated to reflux at 100° C. under argon for 1 hour. The reaction was shown to be complete by LC/MS. The reaction mixture was cooled and the solvent evaporated to dryness. Water and 2N HCl was added to acidify. This was extracted with ethyl acetate (×2), dried over magnesium sulphate and evaporated to a solid which was dried overnight in a vacuum oven to give the title compound (0.038 g, 0.09 mmol).

LC/MS: Rt=3.14, [MH]+ 424

The following compounds were prepared in a similar manner to {4-[4,9-bis(ethyloxy)-1-oxo-1,3-dihydro-2H-benzo[f]isoindol-2-yl]-3-fluorophenyl}acetic acid, using the appropriate starting materials.

| Example | | Name | LC/MS |
|---|---|---|---|
| Example 5 | | {2-Fluoro-4-[1-oxo-4,9-bis(propyloxy)-1,3-dihydro-2H-benzo[f]isoindol-2-yl]phenyl}acetic acid | Rt = 3.75 [MH]+ 452 |
| Example 6 | | (4-{4,9-Bis(1-methylethoxy)-1-oxo-1,3-dihydro-2H-benzo[f]isoindol-2-yl}-2-fluorophenyl)acetic acid | Rt = 3.60 [MH]+ 452 |
| Example 7 | | {3-Fluoro-4-[1-oxo-4,9-bis(propyloxy)-1,3-dihydro-2H-benzo[f]isoindol-2-yl]phenyl}acetic acid | Rt = 3.52 [MH]+ 452 |
| Example 8 | | (4-{4,9-Bis(1-methylethoxy)-1-oxo-1,3-dihydro-2H-benzo[f]isoindol-2-yl}-3-fluorophenyl)acetic acid | Rt = 3.36 [MH]+ 452 |

Example 9

{4-[4,9-Bis(ethyloxy)-1-oxo-1,3-dihydro-2H-benzo[f]isoindol-2-yl]-2-fluorophenyl}acetic acid

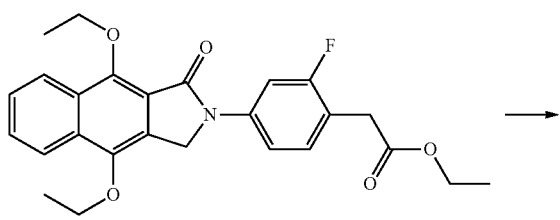

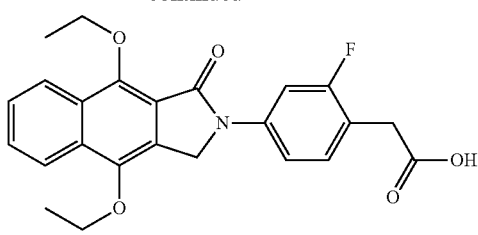

Ethyl {4-[4,9-bis(ethyloxy)-1-oxo-1,3-dihydro-2H-benzo[f]isoindol-2-yl]-2-fluorophenyl}acetate (20.2 g, 44.8 mmol) was suspended in ethanol (450 ml) and treated with 2N sodium hydroxide (150 ml). The mixture was heated under reflux for 1 hour then cooled, and concentrated in vacuo to ~200 ml, then acidified with 2N hydrochloric acid. The white solid was collected by filtration, washed with water (500 ml)

and dried in a vacuum oven to yield the title compound as a cream solid (18.45 g, 43.6 mmol).

LC/MS: Rt=3.35, [MH]⁺ 424

¹H-NMR (DMSO) δ12.49 (1H, br, s), δ8.32 (1H, d, J=8 Hz), δ8.19 (1H, d, J=8 Hz), δ7.96 (1H, dd, J=13, 2 Hz), δ7.74 (1H, dd, J=9, 2 Hz), δ 7.71 (1H, t, 8 Hz), δ7.64 (1H, t, 8 Hz), δ7.41 (1H, t, 9 Hz), δ5.19 (2H, s), δ4.39 (2H, q, J=7 Hz), δ4.32 (2H, q, 7 Hz), δ3.63 (2H, s), δ1.48 (3H, t, J=7 Hz), δ1.46 (3H, t, J=7 Hz).

Description 15

Diethyl (3,5-difluoro-4-nitrophenyl)propanedioate

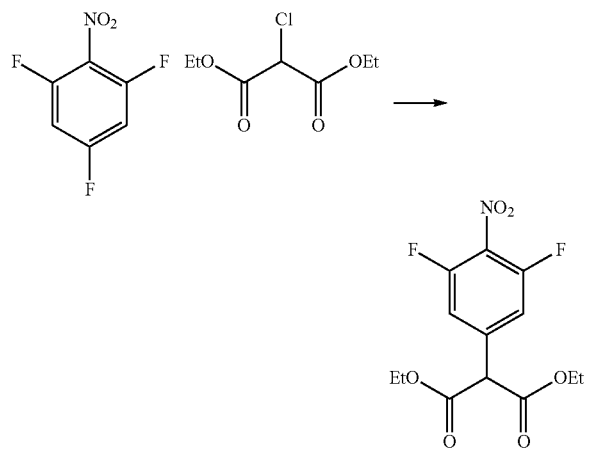

To a solution of 1,3-nitrobenzene (3.0 g, 16.95 mmol) and diethyl chloropropanedioate (3.3 g, 16.95 mmol) in DMF (20 ml) cooled in an ice bath was added crushed sodium hydroxide (1.36 g, 33.90 mmol) in portions. This resulted in a bright red solution. The reaction was stirred at room temperature overnight. This was then acidified with 2N HCl (50 ml) and extracted ×2 with ethyl acetate (100 ml). The combined organics were washed with brine (100 ml), dried over magnesium sulphate, filtered and evaporated. The residue was purified by chromatography eluting with 5-40% ethyl acetate in hexane. The cleanest fractions were evaporated to give the title compound as a yellow solid (2.08 g, 6.56 mmol). LC/MS: Rt=3.06, [MH]⁺ 318.

Description 16

Diethyl (4-amino-3,5-difluorophenyl)propanedioate

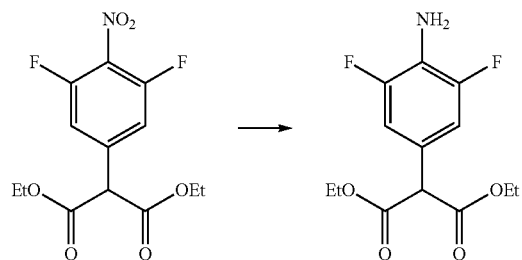

Diethyl (3,5-difluoro-4-nitrophenyl)propanedioate (2.08 g, 6.56 mmol) was added to ethanol (100 ml). 10% Palladium on carbon (wet paste) (0.208 g) was then added under a flow of argon. This was treated with ammonium formate (2.07 g, 32.80 mmol) and the reaction heated to reflux for 30 minutes. Once cooled to room temperature the mixture was filtered through celite and washed with ethanol. This was evaporated to a brown oily solid. Triturating in DCM removed insoluble impurities. The liquors were evaporated and then purified by chromatography eluting with 5-40% ethyl acetate in hexane. The clean fractions were evaporated to give the title compound as a pale brown oil (0.774 g, 2.70 mmol). LC/MS: Rt=2.69, [MH]⁺ 288.

Description 17

Ethyl (4-amino-3,5-difluorophenyl)acetate

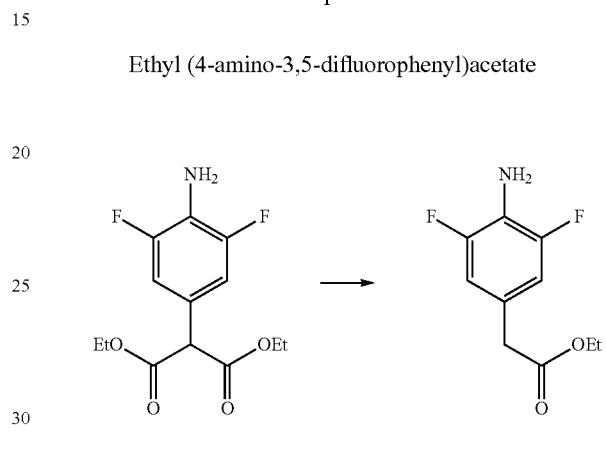

Diethyl (4-amino-3,5-difluorophenyl)propanedioate (0.770 g, 2.68 mmol) was dissolved in ethanol (50 ml) and treated with sodium hydroxide (0.107 g, 2.68 mmol) in water (1.5 ml). This was heated to 90° C. for 55 minutes. Further sodium hydroxide (0.016 g, 0.40 mmol) was added to the reaction and heating continued for 15 minutes. The mixture was cooled to room temperature and evaporated. This was acidified with 2N HCl (20 ml) and extracted ×2 with ethyl acetate (25 ml). The combined organics were washed with brine (50 ml), dried over magnesium sulphate, filtered and evaporated to give the title compound as a pale brown oil (0.610 mg, 2.84 mmol, >100%). LC/MS: Rt=2.52, [MH]⁺ 216.

Example 10

{4-[4,9-Bis(ethyloxy)-1,3-dioxo-1,3-dihydro-2H-benzo[f]isoindol-2-yl]-3,5-difluorophenyl}acetic acid and ethyl {4-[4,9-bis(ethyloxy)-1,3-dioxo-1,3-dihydro-2H-benzo[f]isoindol-2-yl]-3,5-difluorophenyl}acetate

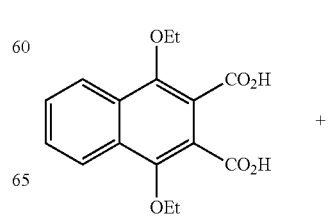

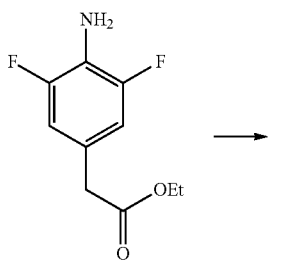

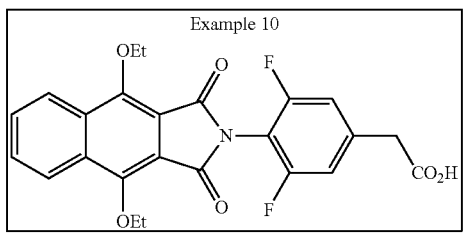

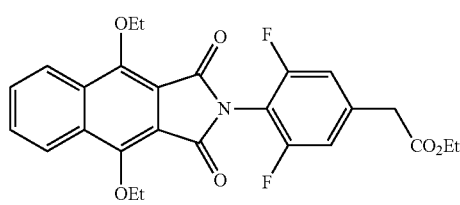

To a solution of 1,4-bis(ethyloxy)-2,3-naphthalenedicarboxylic acid* (0.389 g, 1.28 mmol) in acetic acid (5 ml), was added ethyl (4-amino-3,5-difluorophenyl)acetate (0.55 g, 2.56 mmol) and DMAP (0.047 g, 0.38 mmol). The reaction was heated to 120° C. for two days. Water (15 ml) was added to the mixture and the resulting cream solid was collected by filtration and washed with water. This was dried in the vacuum oven. The crude mixture was purified using reverse phase chromatography.

The most polar fractions were combined to give two batches of the acid, Example 10, {4-[4,9-bis(ethyloxy)-1,3-dioxo-1,3-dihydro-2H-benzo[f]isoindol-2-yl]-3,5-difluorophenyl}acetic acid (0.131 g, 0.29 mmol) LC/MS: Rt=3.30, [MH]+ 456 and (0.05 g, 0.11 mmol) LC/MS: Rt=3.30, [MH]+ 456.

Less polar fractions were combined as a mixture of the acid and ethyl ester. These were evaporated and purified further using normal phase chromatography eluting with 7-60% ethyl acetate in hexane. The fractions were evaporated to give two batches of the ethyl ester as a pale yellow solid, ethyl {4-[4,9-bis(ethyloxy)-1,3-dioxo-1,3-dihydro-2H-benzo[f]isoindol-2-yl]-3,5-difluorophenyl}acetate (0.172 g, 0.36 mmol) LC/MS: Rt=3.90, [MH]+ 484 and (0.072 g, 0.15 mmol) LC/MS: Rt=3.72, [MH]+ 484.

*1,4-bis(ethyloxy)-2,3-naphthalenedicarboxylic acid may be prepared in accordance with the method disclosed in International Patent Application, Publication Number WO02/064564.

Description 18

Ethyl {4-[4,9-bis(ethyloxy)-1-hydroxy-3-oxo-1,3-dihydro-2H-benzo[f]isoindol-2-yl]-3,5-difluorophenyl}acetate

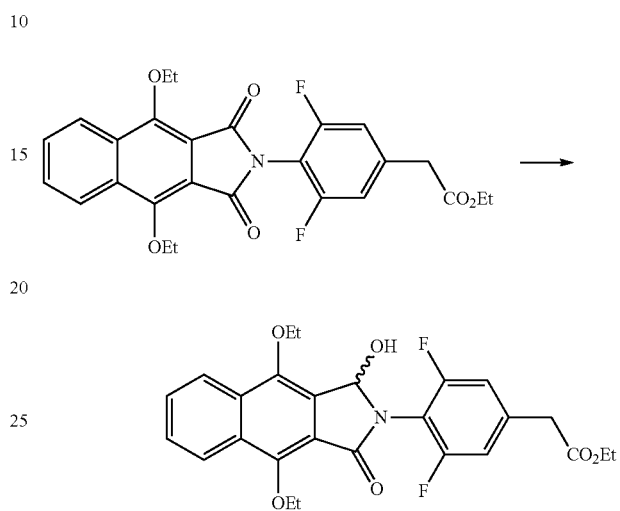

To a stirred solution of ethyl {4-[4,9-bis(ethyloxy)-1,3-dioxo-1,3-dihydro-2H-benzo[f]isoindol-2-yl]-3,5-difluorophenyl}acetate (0.240 g, 0.50 mmol) in THF (10 ml) and methanol (5 ml) was added sodium borohydride (0.019 g, 0.50 mmol) slowly under an argon atmosphere. This was stirred at room temperature for 15 minutes, and then a further 0.057 g (1.50 mmol) of sodium borohydride was added to drive the reaction to completion. After 1.5 hours the reaction was evaporated and quenched with an aqueous solution of ammonium chloride. This was extracted ×2 with ethyl acetate (25 ml) and the combined extracts washed with brine. The organics layer was then dried over magnesium sulphate, filtered and evaporated to give the title compound as a yellow oily solid (0.240 g, 0.49 mmol) LC/MS: Rt=3.42 and 3.46, [MH]+ 486.

Description 19

Ethyl {4-[4,9-bis(ethyloxy)-1-oxo-1,3-dihydro-2H-benzo[f]isoindol-2-yl]-3,5-difluorophenyl}acetate

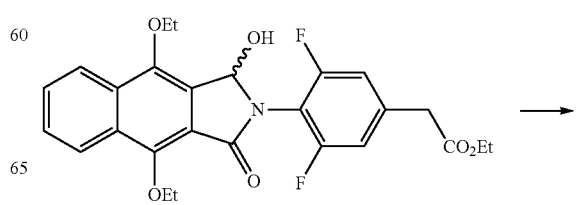

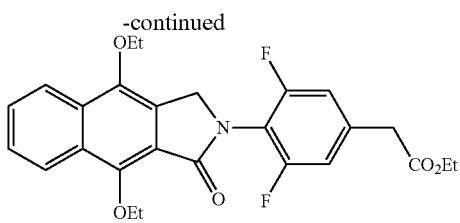

To a stirred solution of ethyl {4-[4,9-bis(ethyloxy)-1-hydroxy-3-oxo-1,3-dihydro-2H-benzo[f]isoindol-2-yl]-3,5-difluorophenyl}acetate (0.240 g, 0.495 mmol) in TFA (3 ml) at 0° C. was added triethylsilane (0.118 ml, 0.742 mmol) drop wise. The bright red solution turned light yellow on addition. The mixture was evaporated then purified by MDAP. The fractions were evaporated to give a yellow solid (0.049 g, 0.10 mmol) LC/MS: Rt=3.62, [MH]+ 470.

Example 11

{4-[4,9-Bis(ethyloxy)-1-oxo-1,3-dihydro-2H-benzo[f]isoindol-2-yl]-3,5-difluorophenyl}acetic acid

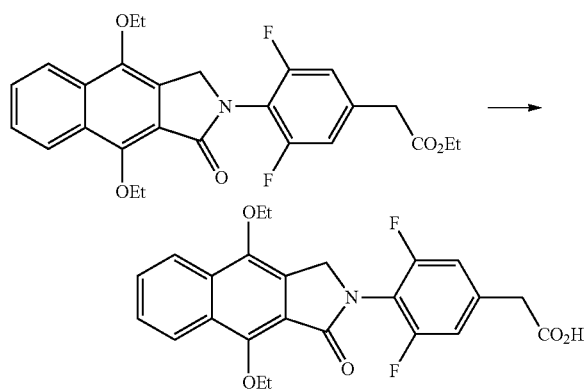

To ethyl {4-[4,9-bis(ethyloxy)-1-oxo-1,3-dihydro-2H-benzo[f]isoindol-2-yl]-3,5-difluorophenyl}acetate (0.045 g, 0.096 mml) was added acetic acid (3 ml) and 2N hydrochloric acid (3 ml). This was heated to 100° C. for 1 hour. Heating was stopped and the reaction was cooled to room temperature, water added and the resulting yellow solid collected by filtration and dried in the vac oven. This was purified by MDAP (Shallow gradient). The clean fraction was evaporated down to give the title compound as a clear glass (0.018 g, 0.04 mmol) LC/MS: Rt=3.16, [MH]+ 442.

{4-[4,9-Bis(ethyloxy)-1-oxo-1,3-dihydro-2H-benzo[f]isoindol-2-yl]-2-fluorophenyl}Acetic Acid (Example 9) was Also Prepared According to the Following Procedures Step 1

Diethyl 1,4-dihydroxy-2,3-naphthalenedicarboxylate

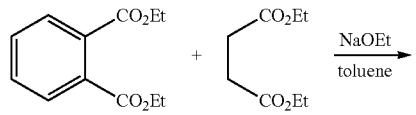

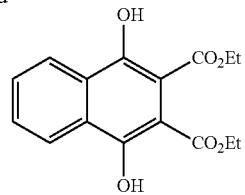

To a stirred suspension of sodium ethoxide (95%, 725 g, 10.2 mol) in toluene (7.2 L, azeotroped to remove water) was added diethyl phthalate (1513 mL, 7.6 mol) under a nitrogen atmosphere. The resulting suspension was heated to 70° C. followed by the dropwise addition of diethyl succinate (800 mL, 5.07 mol) over a period of one hour. The reaction mixture was then stirred at 70° C. under a nitrogen atmosphere for 18 hours, with the consumption of diethyl succinate monitored by TLC analysis (silica, dichloromethane). The reaction mixture was cooled to 5° C., water (7.2 L) added dropwise and the suspension agitated for 5 minutes before stirring was stopped and the layers allowed to separate. The aqueous layer was collected and adjusted to pH 4.5 by dropwise addition of concentrated hydrochloric acid (~600 mL) at 5° C.*. The precipitated solid was isolated by filtration, washed with water (2 L) and freeze-dried to give the crude product as a yellow solid (520 g, 34% yield).

*The aqueous mixture should be acidified as soon as feasible to avoid hydrolysis of the desired product.

Step 2

Diethyl 1,4-bis(ethyloxy)-2,3-naphthalenedicarboxylate

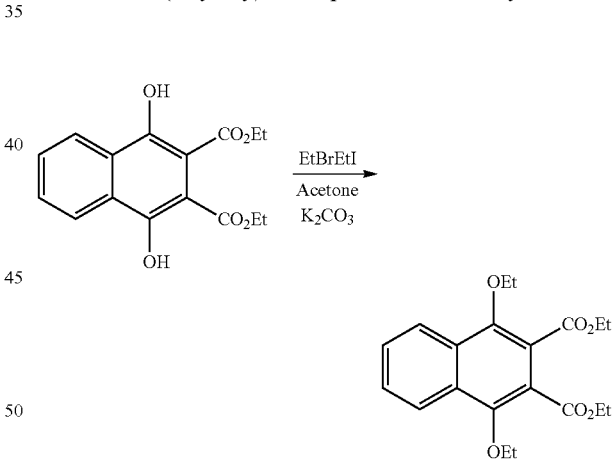

A suspension of potassium carbonate (1728 g, 12.5 mol) in acetone (11 L) was stirred at 40° C. for two hours, then allowed to cool to 20° C. Diethyl 1,4-bis(ethyloxy)-2,3-naphthalenedicarboxylate (1087 g, 3.57 mol) and ethyl bromide* (800 mL, 10.7 mol) were added to the reaction mixture. This was followed by heating to reflux for 18 hours. $^1$H-nmr spectroscopy indicated predominantly mono-alkylation so the reaction mixture was allowed to cool to ~30° C., ethyl iodide (470 mL, 5.88 mol) was added and then the mixture heated to reflux for a further 24 hours. The reaction mixture was cooled to room temperature, filtered and the inorganic solids washed with acetone (3 L). Removal of solvent from the combined filtrates under reduced pressure gave the desired product as a dark red solid (1343 g, quantitative yield).

*Ethyl iodide may also be used in this reaction and may be preferable on a large scale due to the low boiling point of ethyl bromide.

Step 3

1,4-Bis(ethyloxy)-2,3-naphthalenedicarboxylic acid

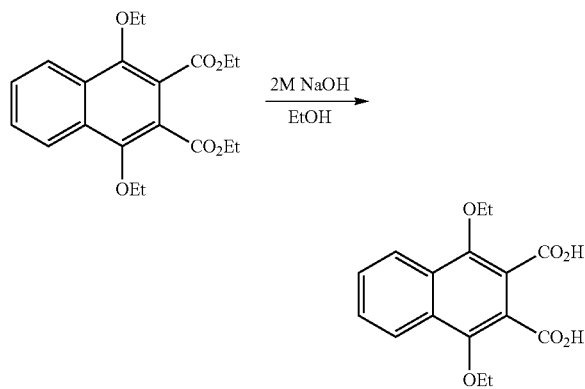

To a stirred solution of diethyl 1,4-bis(ethyloxy)-2,3-naphthalenedicarboxylate (1343 g, 3.73 mol) in ethanol (5.5 L) was added 2M sodium hydroxide solution (5.5 L, 11.0 mol). The reaction mixture was heated to reflux for 8 hours, with the reaction progress monitored by $^1$H-nmr spectroscopy. The mixture was then cooled to 0° C. for 18 hours before isolation of the crystallised solid by filtration, washing with ethanol (5 L) and drying in a vacuum oven at 60° C. to constant mass gave the desired product as a white solid (903.7 g, ~11% water remains by Karl-Fischer, 62% yield).

Step 4a

Ethyl (4-amino-2-fluorophenyl)acetate

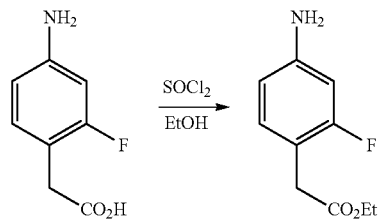

Thionyl chloride (986 mL, 8.51 mol) was added dropwise to a stirred suspension of 2-(4-amino-2-fluorophenyl)acetic acid (960 g, 5.68 mol) in ethanol (10 L) at 0° C. under a nitrogen atmosphere. The reaction mixture was then heated to 40° C. for 48 hours, with the reaction progress monitored by $^1$H-nmr spectroscopy. The reaction mixture was evaporated to dryness and the residue redissolved in a mixture of dichloromethane (8 L) and saturated sodium hydrogen carbonate solution (5 L). Further sodium hydrogen carbonate solution was added (~8 L) until the aqueous phase was basic. The layers were separated and the organic phase washed with saturated sodium hydrogen carbonate solution (4 L), dried over magnesium sulphate and the solvent removed under reduced pressure gave the desired product, ethyl (4-amino-2-fluorophenyl)acetate, as an orange oil (1042 g, 93% yield), that may crystallise upon standing.

Step 4b

Ethyl {4-[4,9-bis(ethyloxy)-1,3-dioxo-1,3-dihydro-2H-benzo[f]isoindol-2-yl]-2-fluorophenyl}acetate

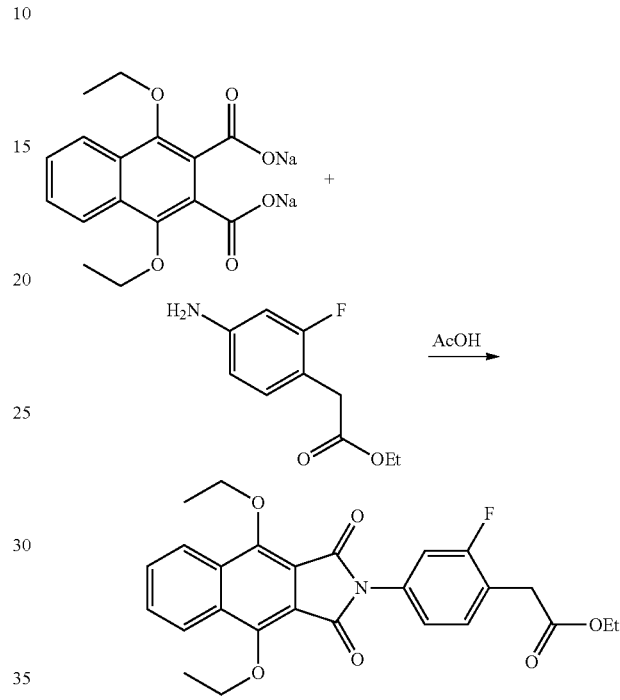

A mixture of 1,4-bis(ethyloxy)-2,3-naphthalenedicarboxylic acid sodium salt (526 g, 1.51 mol) and ethyl (4-amino-2-fluorophenyl)acetate (539 g, 2.73 mol) in glacial acetic acid (5100 mL) was heated to reflux for 6 hours, with reaction progress monitored by $^1$H-nmr spectroscopy. The reaction mixture was allowed to cool to room temperature, stirred for 18 hours, diluted with water (14 L) and stirred for a further 30 minutes. The product was isolated by filtration, washed with water (5 L) and dried in a vacuum oven at 60° C. to give the desired product as an off-white solid (587 g, 84% yield).

Step 5a

Ethyl {4-[4,9-bis(ethyloxy)-1-hydroxy-3-oxo-1,3-dihydro-2H-benzo[f]isoindol-2-yl]-2-fluorophenyl}acetate

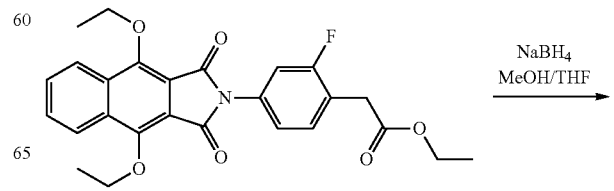

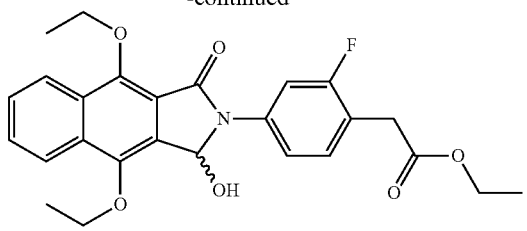

Sodium borohydride (45 g, 1.19 mol) was added portionwise over 45 minutes to a stirred suspension of ethyl {4-[4,9-bis(ethyloxy)-1,3-dioxo-1,3-dihydro-2H-benzo[t]isoindol-2-yl]-2-fluorophenyl}acetate (542 g, 1.16 mol) in a mixture of methanol (1.63 L) and tetrahydrofuran (4.34 L) at between −5 and 0° C. under a nitrogen atmosphere. After stirring for a further 60 minutes at 0° C., additional portions of sodium borohydride (a total of 25 g, 0.66 mol) were added until no more starting material was observable by TLC analysis (silica, hexane:ethyl acetate, 70:30). At this point, the reaction mixture was quenched by dropwise addition of saturated ammonium chloride solution (~2700 mL) to ~pH9. Ethyl acetate (2 L) was added and the mixture agitated for 5 minutes. Stirring was stopped and the layers separated. The aqueous phase was extracted with a further portion of ethyl acetate (2×4 L). The combined organic phases were washed with brine (6 L), dried over magnesium sulphate and filtered. The material was combined with that from another batch processed in a similar manner and evaporated to dryness. The residue was redissolved in dichloromethane (5 L), dried with sodium sulfate, filtered and evaporated to dryness. This was slurried in isopropyl alcohol (2 L) and dried by dissolving in DCM (5 L) and evaporating to dryness three times to give the desired product as an off-white solid (929 g, 89% yield).

Step 5b

Ethyl {4-[4,9-bis(ethyloxy)-1-oxo-1,3-dihydro-2H-benzo[f]isoindol-2-yl]-2-fluorophenyl}acetate

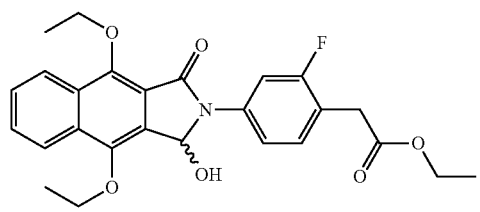

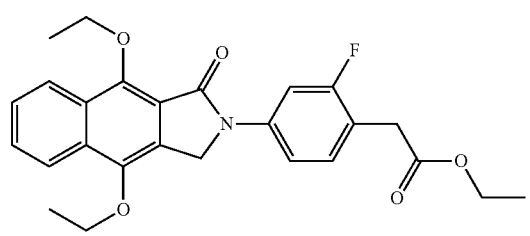

Trifluoroacetic acid (1900 mL) was added to a stirred solution of ethyl {4-[4,9-bis(ethyloxy)-1-hydroxy-3-oxo-1,3-dihydro-2H-benzo[f]isoindol-2-yl]-2-fluorophenyl}acetate (898 g, 1.92 mol) in dichloromethane (1900 mL) at 0° C. under a nitrogen atmosphere. Triethylsilane (465 mL, 2.92 mol) was added dropwise to the deep red solution ensuring that the temperature was maintained below 3° C. The reaction mixture was then stirred at 0° C. for 45 minutes, over which time the solution turned yellow and all ethyl {-4-[4,9-bis(ethyloxy)-1-hydroxy-3-oxo-1,3-dihydro-2H-benzo[f]isoindol-2-yl]-2-fluorophenyl}acetate was shown to be consumed by TLC analysis (silica, dichloromethane:methanol, 99:1). The reaction mixture was evaporated to dryness under reduced pressure, slurried in hexane (2×2.5 L) and then isopropanol (2.5 L) at 40° C. and dried under vacuum to give the desired product as a white solid (821 g, 95% yield).

Step 6a

{4-[4,9-Bis(ethyloxy)-1-oxo-1,3-dihydro-2H-benzo[f]isoindol-2-yl]-2-fluorophenyl}acetic acid

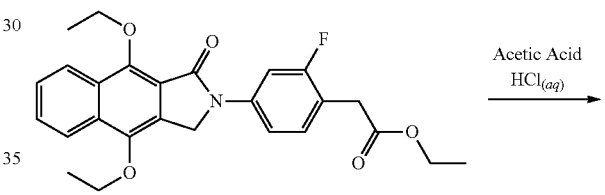

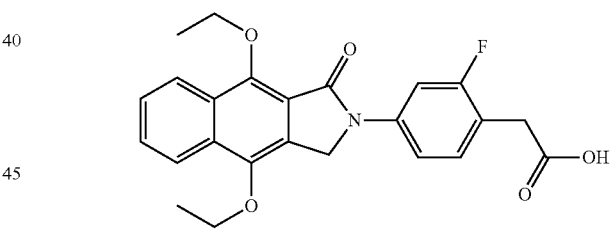

A suspension of ethyl {4-[4,9-bis(ethyloxy)-1-oxo-1,3-dihydro-2H-benzo[t]isoindol-2-yl]-2-fluorophenyl}acetate (70.0 g, 155 mmol) in a mixture of glacial acetic acid (650 mL) and hydrochloric acid (6 M, 250 mL) was heated to reflux under a nitrogen atmosphere, with the reaction progress monitored by TLC analysis (silica, dichloromethane:methanol, 99:1). After 60 minutes the reaction mixture was cooled to 0° C. The precipitated solid was isolated by filtration, washed with water (500 mL), slurried in glacial acetic acid (350 mL) at 50° C. and air dried to give the desired product, {4-[4,9-bis(ethyloxy)-1-oxo-1,3-dihydro-2H-benzo[f]isoindol-2-yl]-2-fluorophenyl}acetic acid, as an off-white solid (57.7 g, 88% yield).

During this reaction procedure all of the solid will dissolve, followed by the product precipitating from the reaction mixture after approximately 30 minutes. A small increase in the ratio of acetic acid to hydrochloric acid may be used to ensure that the reaction entities remain in solution throughout.

Step 6b

{4-[4,9-Bis(ethyloxy)-1-oxo-1,3-dihydro-2H-benzo[f]isoindol-2-yl]-2-fluorophenyl}acetic acid

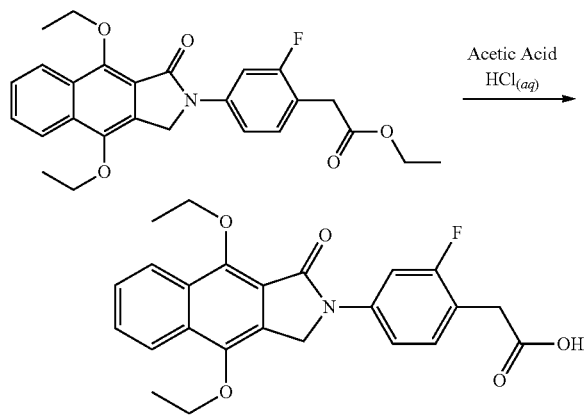

A suspension of ethyl {-4-[4,9-bis(ethyloxy)-1-oxo-1,3-dihydro-2H-benzo[f]isoindol-2-yl]-2-fluorophenyl}acetate (200.0 g, 443 mmol) in a mixture of glacial acetic acid (2080 mL) and hydrochloric acid (2 M, 700 mL) was heated to reflux under a nitrogen atmosphere, with the reaction progress monitored by TLC analysis (silica, dichloromethane:methanol, 99:1). After 60 minutes the reaction mixture was cooled to 0° C. The precipitated solid was isolated by filtration, washed with water (1400 mL), and freeze-dried to give the desired product as an off-white solid (163.4 g, 87% yield).

The final product batch was obtained by an ethyl acetate slurry (3 L) of five batches performed as above (total mass, 555 g) then freeze-drying and oven drying at 70° C. to give the desired product, {4-[4,9-bis(ethyloxy)-1-oxo-1,3-dihydro-2H-benzo[f]isoindol-2-yl]-2-fluorophenyl}acetic acid, as an off-white solid (510.6 g, 82% yield for hydrolysis and slurry).

Biological Data

In Vitro cAMP Assay

Studies were performed using HEK-293(T) cells expressing the recombinant human prostanoid $EP_4$ receptor (HEK-$EP_4$ cells). Cells were grown as a monolayer culture in DMEM-F12/F12 containing glutamax II (Gibco) and supplemented with 10% foetal bovine serum (Gibco) and 0.4 mg.ml-1 G418. HEK-$EP_4$ cells were pre-treated 24 hr and 30 mins prior to the experiment with 10 μM indomethacin and harvested using Versene containing 10 μM indomethacin. The cells were resuspended in assay buffer (DMEM:F12, 10 μM indomethacin and 200 μM IBMX) at $1 \times 10^6$ cells per ml and incubated for 20 min at 37° C. Thereafter, 50 μl of cells were added to 50 μl agonist (compound of Formula (I)) and incubated at 37° C. for 4 minutes before stopping reactions with 1000 of 1% triton X-100. cAMP levels in the cell lysates were determined using a competition binding assay. In this assay the ability of cell lysates to inhibit 3H-cAMP (Amersham) binding to the binding subunit of protein kinase A was measured and cAMP levels were calculated from a standard curve. The data for each compound were expressed as a % of the response to a 10 nM maximal concentration of the standard agonist PGE2. For each compound the maximal response and concentration of compound causing 50% of its maximal response were calculated. Intrinsic activity is expressed relative to the maximal response to PGE2. Unless stated, reagents were purchased commercially from Sigma.

The Examples of the present invention were tested in the above-mentioned assay and exhibited average $pEC_{50}$ values of 6.8 or higher, and average intrinsic activities of 50% or higher. For example, Example 9 exhibited an average $pEC_{50}$ value of 7.4 and an average intrinsic activity of 68% when tested in the above-mentioned assay (n=24).

In Vivo Assay—Effect of {4-[4,9-Bis(ethyloxy)-1-oxo-1,3-dihydro-2H-benzo[f]isoindol-2-yl]-2-fluorophenyl}acetic acid ('Example 9') in an $ED_{20}$ Combination and a Fixed Dose Combination with Paracetamol on FCA Induced Hypersensitivity in the Rat Aim of study:

To determine whether combining Example 9 and paracetamol at $ED_{20}$ doses or as a fixed dose combination will produce synergy in the reversal of the established FCA induced hypersensitivity.

Methods:

FCA and Weight-Bearing Readout

At the start of the study, naïve weight bearing readings were taken. The hypersensitivity to pain was measured using the Rat incapacitance tester (Linton instruments).

All male rats (RH strain, 180-220 g) then received an intraplantar injection of 100 ul of FCA (Freund's complete adjuvant) into the left hind paw. The ECA was sonicated for 15 minutes prior to use.

24 hours after administration of the FCA, pre-dose weight bearing readings were taken. All animals were then ranked and randomised for dosing according to their FCA window (predose difference in grams—naïve difference in grams). Rats with FCA window less than 30 were excluded from the study.

Animals were then dosed orally according to ranking and randomisation. Two studies were carried out as follows:

In the first study the $ED_{20}$ doses of Example 9 and paracetamol were combined using the following protocol,
(1) Vehicle (1% methylcellulose) p.o.
(2) Paracetamol (60 mg/kg) p.o.*
(3) Example 9 (0.1 mg/kg) p.o.*
(4) Example 9 (0.1 mg/kg)+Paracetamol (60 mg/kg) p.o.**
(5) Celecoxib (10 mg/kg) p.o.
*$ED_{20}$ dose
**Example 9 was dosed initially followed by paracetamol 30 minutes later.

In the second study a fixed dose ratio combination with Example 9 and paracetamol was completed using the following protocol,
(1) Vehicle (1% methylcellulose) p.o.+Vehicle (1% methylcellulose) p.o.
(2) Example 9, 0.003 mg/kg p.o.+Paracetamol, 1.8 mg/kg p.o.
(3) Example 9, 0.01 mg/kg p.o.+Paracetamol, 6 mg/kg p.o.
(4) Example 9, 0.03 mg/kg p.o.+Paracetamol, 18 mg/kg p.o.
(5) Example 9, 0.1 mg/kg p.o.+Paracetamol, 60 mg/kg p.o.
(6) Vehicle (1% methylcellulose) p.o.+Celecoxib, 10 mg/kg p.o.

Animals were assessed in the weight bearing apparatus 1 hour after the dose of paracetamol.

The study was blind and randomised by FCA window using a Latin square method.

Preparation Details

All compounds were ground using a pestle and mortar prior to adding the vehicle (1% methylcellulose). Dose volume 5 ml/kg.

All doses were sonicated and stirred before administration.

In this study a positive control was also tested (Celecoxib). If the positive control did not produce a significant reversal of the FCA induced hypersensitivity (>60%) the experiment was deemed invalid and the study repeated.

Statistical Analysis

% reversals were calculated by using the naïve, pre-dose and post dose values as follows: % Reversal=[(Pre-dose−Post-dose)/(Pre-dose−Naïve)]×100.

Graphs and $ED_{50}$ values were calculated using Prism3.

Statistical analysis was carried out using ANOVA and Fischer LSD test from statistical package Statistica 6.

Synergy was statistically calculated using the synergy macro. The $logED_{50}$ values and the Standard errors for the individual molecules and the combination study are obtained from Statistica 6 and put into the macro. The fixed dose ratio is specified and the macro then calculates whether the combination was statistically synergistic. It compares the combination data to the theoretical addition of the individual compounds.

Results:

Percentage Reversal of the Established FCA-Induced Hypersensitivity:

Significant activity was demonstrated. Reversal of hypersensitivity equivalent to a maximally efficacious dose of celecoxib was produced with combinations of low doses of Example 9 and paracetamol which are ineffective when administered alone (FIG. 1). The observed effect has been shown to be synergistic in nature (FIG. 2).

When dosed alone at 3 mg/kg in the same model, Example 9 has an $EC_{50}$ of 0.6 μM and advantageously produced an 80% reversal of eFCA-induced hypersensitivity.

Example 9 also exhibited an oral pharmacokinetic half life of 7.6 hours in the rat.

FIG. 1 illustrates the effect of combining Example 9 (0.1 mg/kg) and paracetamol (60 mg/kg) alone and in combination on FCA-induced hypersensitivity.

FIG. 2 illustrates a theoretical additive dose response curve vs. actual observed dose response curve for an Example 9+paracetamol combination.

The invention claimed is:

1. A compound of formula (I) or a pharmaceutically acceptable salt thereof,

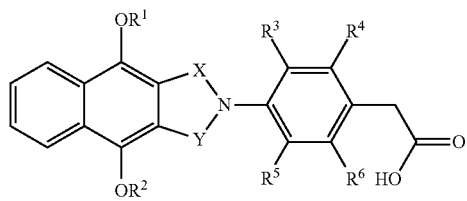

(I)

wherein, $R^1$ and $R^2$ independently represent $C_{1-4}$ alkyl;

$R^3$, $R^4$, $R^5$ and $R^6$ independently represent H or F, provided that, at least one of $R^3$ and $R^4$ represents H, at least one of $R^5$ and $R^6$ represents H, and at least one of $R^3$, $R^4$, $R^5$ and $R^6$ represents F; and X and Y independently represent $CH_2$ or C=O, provided that at least one of X and Y represents C=O.

2. A compound of formula (I), according to claim 1, wherein $R^1$ and $R^2$ are the same and represent $C_{1-4}$ alkyl.

3. A compound of formula (I), according to claim 1, wherein $R^1$ and $R^2$ are independently selected from the group consisting of ethyl, n-propyl and iso-propyl.

4. A compound of formula (I), according to claim 1, wherein both X and Y represent C=O.

5. A compound of formula (I), according to claim 1, wherein $R^3$ represents F and $R^4$, $R^5$ and $R^6$ represent H.

6. A compound of formula (I), according to claim 1, wherein $R^4$ represents F and $R^3$, $R^5$ and $R^6$ represent H.

7. A compound of formula (I), according to claim 1, wherein $R^3$ and $R^5$ represent F and $R^4$ and $R^6$ represent H.

8. A compound according to claim 1, of formula (IA), or a pharmaceutically acceptable salt thereof,

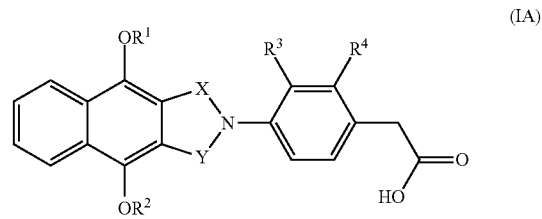

(IA)

wherein, $R^1$ and $R^2$ independently represent $C_{1-4}$ alkyl;

$R^3$ and $R^4$ independently represent H or F provided that they are not the same; and X and Y independently represent $CH_2$ or C=O provided that at least one of X and Y represents C=O.

9. A compound of formula (I), according to claim 1, selected from the group consisting of:

{4-[4,9-Bis(ethyloxy)-1,3-dioxo-1,3-dihydro-2H-benzo[f]isoindol-2-yl]-3-fluorophenyl}acetic acid;

{4-[1,3-Dioxo-4,9-bis(propyloxy)-1,3-dihydro-2H-benzo[f]isoindol-2-yl]-3-fluorophenyl}acetic acid;

(4-{4,9-Bis(1-methylethoxy)-1,3-dioxo-1,3-dihydro-2H-benzo[f]isoindol-2-yl}-3-fluorophenyl)acetic acid;

{-4-[4,9-Bis(ethyloxy)-1-oxo-1,3-dihydro-2H-benzo[f]isoindol-2-yl]-3-fluorophenyl}acetic acid;

{-4-[4,9-Bis(ethyloxy)-1-oxo-1,3-dihydro-2H-benzo[f]isoindol-2-yl]-2-fluorophenyl}acetic acid;

{2-Fluoro-4-[1-oxo-4,9-bis(propyloxy)-1,3-dihydro-2H-benzo[f]isoindol-2-yl]phenyl}acetic acid;

(4-{4,9-Bis(1-methylethoxy)-1-oxo-1,3-dihydro-2H-benzo[f]isoindol-2-yl}-2-fluorophenyl)acetic acid;

{3-Fluoro-4-[1-oxo-4,9-bis(propyloxy)-1,3-dihydro-2H-benzo[f]isoindol-2-yl]phenyl}acetic acid; and (4-{4,9-Bis(1-methylethoxy)-1-oxo-1,3-dihydro-2H-benzo[f]isoindol-2-yl}-3-fluorophenyl)acetic acid;

{-4-[4,9-Bis(ethyloxy)-1,3-dioxo-1,3-dihydro-2H-benzo[f]isoindol-2-yl]-3,5-difluorophenyl}acetic acid;

{4-[4,9-Bis(ethyloxy)-1-oxo-1,3-dihydro-2H-benzo[f]isoindol-2-yl]-3,5-difluorophenyl}acetic acid; or a pharmaceutically acceptable salt thereof.

10. A compound that is ({-4-[4,9-Bis(ethyloxy)-1-oxo-1,3-dihydro-2H-benzo[f]isoindol-2-yl]-2-fluorophenyl}acetic acid, having the structure:

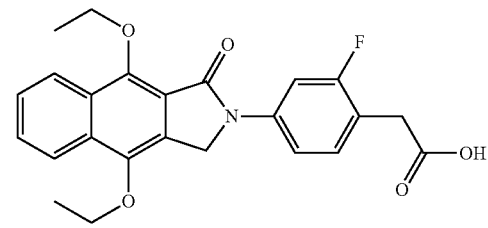

or a pharmaceutically acceptable salt thereof.

11. A pharmaceutical composition comprising a compound of formula (I) or a pharmaceutically acceptable salt thereof according to claim 1 and a pharmaceutically acceptable carrier or diluent therefor.

* * * * *